(12) United States Patent
Mims et al.

(10) Patent No.: US 12,310,578 B2
(45) Date of Patent: May 27, 2025

(54) ENDOSCOPIC SUTURE LOOP ANCHORS AND METHODS

(71) Applicant: BOSTON SCIENTIFIC SCIMED, INC., Maple Grove, MN (US)

(72) Inventors: John Mims, Austin, TX (US); Charles Dean, Austin, TX (US); Nicole Pinto, Austin, TX (US); Mitchell Gilkey, Austin, TX (US); Vladimir Mitelberg, Austin, TX (US); Donald K. Jones, Dripping Springs, TX (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 89 days.

(21) Appl. No.: 18/141,706

(22) Filed: May 1, 2023

(65) Prior Publication Data

US 2023/0263516 A1 Aug. 24, 2023

Related U.S. Application Data

(60) Continuation of application No. 16/867,072, filed on May 5, 2020, now Pat. No. 11,672,525, which is a
(Continued)

(51) Int. Cl.
*A61B 17/04* (2006.01)
*A61B 17/00* (2006.01)
(Continued)

(52) U.S. Cl.
CPC ...... *A61B 17/0469* (2013.01); *A61B 17/0482* (2013.01); *A61B 17/0485* (2013.01);
(Continued)

(58) Field of Classification Search
CPC ............ A61B 17/0469; A61B 17/0482; A61B 17/0485; A61B 17/0487; A61B 17/06061;
(Continued)

(56) References Cited

U.S. PATENT DOCUMENTS

| 5,259,846 A | 11/1993 | Granger et al. |
| 6,056,771 A | 5/2000 | Proto |

(Continued)

*Primary Examiner* — Jocelin C Tanner
(74) *Attorney, Agent, or Firm* — Seager, Tufte & Wickhem, LLP

(57) ABSTRACT

A suture needle system includes a first needle and at least one second needle. Each of the first and second needles preferably has a common needle body construct. The first needle includes an elongate suture having a length sufficient to extend at least the length of an instrument channel of an endoscope. The second needle includes an opening formed by a loop of suture at which the second needle can be advanced over the elongate suture. In use, the first needle is secured to a first tissue location using an endoscopic suturing system. A second needle is advanced at its opening over the elongate suture and secured to a second tissue location. Additional second needles may be advanced over the elongate suture to respective tissue locations. The elongate suture is pulled taut, drawing the second needles into proximity, and secured.

20 Claims, 33 Drawing Sheets

Related U.S. Application Data division of application No. 15/336,024, filed on Oct. 27, 2016, now Pat. No. 10,639,028.

(60) Provisional application No. 62/248,081, filed on Oct. 29, 2015.

(51) Int. Cl.
*A61B 17/06* (2006.01)
*A61B 17/062* (2006.01)
*A61B 17/29* (2006.01)
*A61F 5/00* (2006.01)

(52) U.S. Cl.
CPC .... *A61B 17/0487* (2013.01); *A61B 17/06061* (2013.01); *A61B 17/06109* (2013.01); *A61B 17/06166* (2013.01); *A61B 17/0625* (2013.01); *A61B 17/29* (2013.01); *A61F 5/0089* (2013.01); *A61B 2017/00004* (2013.01); *A61B 2017/00296* (2013.01); *A61B 2017/00818* (2013.01); *A61B 2017/0417* (2013.01); *A61B 2017/0472* (2013.01); *A61B 2017/0496* (2013.01); *A61B 2017/06052* (2013.01); *A61B 2017/06176* (2013.01)

(58) Field of Classification Search
CPC ........ A61B 17/06109; A61B 17/06166; A61B 17/0625; A61B 17/29; A61B 2017/00004; A61B 2017/00296; A61B 2017/00818; A61B 2017/0417; A61B 2017/0472; A61B 2017/0496; A61B 2017/06052; A61B 2017/06176; A61F 5/0089

USPC ........................................................ 606/147
See application file for complete search history.

(56) References Cited

U.S. PATENT DOCUMENTS

| | | |
|---|---|---|
| 6,494,888 B1 | 12/2002 | Laufer et al. |
| 6,506,196 B1 | 1/2003 | Laufer |
| 6,663,639 B1 | 12/2003 | Laufer et al. |
| 6,821,285 B2 | 11/2004 | Laufer et al. |
| 7,857,823 B2 | 12/2010 | Laufer et al. |
| 8,066,718 B2 | 11/2011 | Weisel et al. |
| 8,277,468 B2 | 10/2012 | Laufer et al. |
| 8,679,136 B2 | 3/2014 | Mitelberg |
| 9,055,940 B2 | 6/2015 | Chin |
| 2003/0171778 A1 | 9/2003 | Lizardi |
| 2004/0106949 A1 | 6/2004 | Cohn et al. |
| 2007/0276408 A1 | 11/2007 | Filipi et al. |
| 2008/0188893 A1 | 8/2008 | Selvitelli et al. |
| 2009/0043335 A1 | 2/2009 | Capurro |
| 2009/0312775 A1* | 12/2009 | Gilkey ................. A61B 17/068 606/147 |
| 2012/0149979 A1 | 6/2012 | Mitelberg |
| 2012/0150200 A1 | 6/2012 | Mitelberg |
| 2013/0066340 A1 | 3/2013 | Pantages et al. |
| 2013/0096612 A1 | 4/2013 | Zajac et al. |
| 2013/0245645 A1 | 9/2013 | Kostrzewski |
| 2014/0257027 A1* | 9/2014 | Palmisano ............ A61F 2/0063 600/37 |
| 2015/0126983 A1 | 5/2015 | Alvarado et al. |

\* cited by examiner

ENDOSCOPIC SUTURE LOOP ANCHORS AND METHODS

CROSS-REFERENCE TO RELATED APPLICATION

This application is a continuation of U.S. Ser. No. 16/867,072, filed May 5, 2020, which is a divisional of U.S. Ser. No. 15/336,024, filed Oct. 27, 2016, which claims the benefit of priority under 35 U.S.C. § 119 to U.S. provisional application Ser. No. 62/248,081, filed Oct. 29, 2015, which applications are hereby incorporated herein by reference in their entireties.

BACKGROUND OF THE INVENTION

1. Field of the Invention

The present invention relates to a treatment device that can be inserted into a body through a natural orifice with an endoscope or other steerable guide member. The present invention may be used to perform suturing on the tissue of a mammal, whether human or not, and whether or not alive, but is not limited thereto.

2. State of the Art

Referring to Prior Art FIG. 1, co-owned U.S. Pat. No. 8,679,136 to Mitelberg describes an endoscopic treatment system 710 including an endoscopic treatment device 720. The device 720 has a structure enabling a small profile for delivery into the body of the patient while providing both a large opening and closing angle and producing a large needle force for piercing tissue to perform a surgical operation such as tissue approximation and suturing within the body. The endoscopic treatment device is used to perform treatment in a body while being operated outside the body. The treatment device 712 includes a flexible member 732 coupled to a proximal handle assembly 722 for operation of the flexible member from outside of the body, and a distal cap assembly 733 adapted to engage the distal end of an endoscope 714. Referring to Prior Art FIGS. 2 and 3, the flexible member 732 is connected to a link mechanism 735 and is actuated to cause a needle holder arm 740 and needle 741 retained therein to move in a direction to puncture tissue and a direction to be removed from tissue.

The cap assembly 733 is adapted to be positioned at the distal end of an endoscope. A transmission member (not shown) extends through the flexible member 732 and has a distal end portion that is inserted into a body and is capable of being operated outside the body by a proximal portion coupled to the handle assembly 722. A push rod 749 is coupled to the distal end portion of the transmission member. A needle holder arm 740 is coupled to the push rod 749 and pivotally coupled to a mounting bracket 738. A removable needle assembly 741 with a length of suture 748 attached thereto is connected to the needle holder arm 740 and is adapted to pierce tissue. Referring to FIGS. 2 through 5, when the push rod 744 is actuated by the transmission member within the flexible member 732, the needle holder arm 740 is moved in a closing direction to cause the needle assembly 741 to pierce tissue (Prior Art FIGS. 4 and 5), or in an opposite opening direction (Prior Art FIGS. 2 and 3).

Turning to Prior Art FIGS. 6 through 9, the needle assembly 741 includes a needle 800 and an elongate length of suture 748. The needle 800 has a needle tip member 802 and a needle base member 803. The needle tip member 802 has a sharpened end 810 which is adapted to pierce tissue and an opposite end 817 provided with a groove 814 that is received in the needle base member 803, and stop 816 that limits insertion of the tip member 802 into the base member 803. Between the end 810 and the groove 814, the tip member includes a second groove 812, which aids in removal of the needle assembly 741 from the needle holder arm 740. The needle base member 803 is a tubular element having axial openings at each of its ends. One open end is adapted to receive end 817 of the tip member 802, and the other open end is adapted to receive the needle holder arm 740. The tubular wall of the base member 803 includes at least one first laser cut tab 804 that is deformed inwardly into the groove 814 to permanently engage the end 817 of the tip member into an assembled structure. The base member 803 includes an opening 809 in its sidewall to receive a portion 818 of the suture 748 and at least one second laser cut tab 806 deformed inwardly into engagement with the received portion 818 of the suture 748 to secure the suture to the needle. The base member 803 at least one third laser cut tab 808 that is deformed inwardly to allow removable engagement between the needle assembly 741 and the needle holder 740 received into its respective open end (Prior Art FIG. 9).

Turning to Prior Art FIG. 10, the endoscopic treatment system includes a needle exchange device 730. The elongate needle exchange device 730 is positioned within a first instrument channel of the endoscope and has a distal end 750 adapted to deliver the needle assembly 741 to the needle holder arm 740 (FIG. 9), and receive and grasp the needle assembly 741 when the needle holder arm 740 is pivoted to a closed position.

Referring to Prior Art FIG. 11, the endoscopic treatment system also includes a tissue-grasping member 900. The tissue-grasping member 900 takes the form of an elongate sheath 910 having proximal and distal ends and is positioned with a second instrument channel of the endoscope. The distal end of the tissue-grasping member may take the form of a helix or tapered spiral 918 in which rotation of the helix when at a desired site adjacent tissue causes the helix to substantially engage the tissue and allow the tissue to be retracted. The proximal end of the tissue-grasping member 900 includes a handle 912 having a main body 914 coupled to the sheath 910 and a rotatable knob 916 for rotating the helix 918 relative to the sheath 910.

The use of the endoscopic suturing system is described in accord with a suturing method. The method includes the steps of:
(1) inserting the cap assembly 733 having a suturing device, the cap assembly coupled to a distal end of an endoscope 712, into the patient's body (Prior Art FIG. 12);
(2) opening a needle arm 740 of the suturing device, the needle arm provided with a removable needle 741 (Prior Art FIG. 12);
(3) engaging a tissue 794 at a desired suture site 796 using the tissue grasper 918 and drawing the tissue back into an intended path of the needle 741 (Prior Art FIGS. 13 and 14);
(4) operating the suturing device to close the needle 741 against the tissue 794 at the desired suture site 796, pierce the tissue, and pass the needle through the tissue (Prior Art FIG. 15);
(5) capturing the needle in the needle exchange device and removing the needle from the tissue (occurring in Prior Art FIG. 15); and (6) then opening the needle arm 740 to remove it from tissue 794 and then releasing the tissue from the tissue grasper 918 (Prior Art FIG. 16).

The suturing device is then relocated to another target location, loaded with another needle, and operated in the same manner to provide a suture at the next target location. The process is repeated as needed to perform a required procedure.

In co-owned U.S. Pub. No. 2015-0126983, an endoscopic suturing system of the type described above is taught for use in a performing an incisionless endoluminal treatment for obesity. In this endoscopic treatment, the gastric tissue is approximated at selected locations and sutured together to reduce the stomach capacity. More particularly, the gastric tissue is gathered in a helical pattern, causing the lateral portion of the stomach; i.e., that portion extending along the greater curve of the stomach, to be drawn in or collapsed inward, to thereby remove such portion of the greater curve from the usable volume of the stomach while maintaining a usable pathway from the esophagus to the pylorus. Even more particularly, the pattern is initiated below the fundus and at a distal portion of the stomach, and a helical suture pattern is advanced around the lateral stomach tissue in a proximal to distal direction. Once the suture is inserted in the helical pattern, it is cinched to draw the tissue together, and then secured. The process is then repeated for another suture at a relatively proximal location. With repeated placement of sutures and subsequent cinching thereof, the cinched suture pattern causes the lateral side (L) of the stomach; i.e., that portion extending along the greater curvature of the stomach, to be drawn in or collapsed inward (toward the medial side (M)) to thereby remove such portion of the greater curvature from the usable volume of the stomach while maintaining a pathway from the esophagus to the pylorus.

While the gastric reduction treatment described in U.S. Pub. No. 2015-0126983 has shown great promise, there are aspects that can be improved. For one, it has been noted that as the tissue is approximated and the stomach capacity is reduced, the surgeon's working area and visibility are limited. This can result in a challenging procedure for less experienced surgeons. Therefore, increased visibility and orientation are desirable. It also would be advantageous to be able to facilitate new stitching patterns that may be more durable but not feasible with the current suturing methods and implements for performing such methods.

SUMMARY OF THE INVENTION

In accord with several aspects of the invention, suture needle systems and kits, and methods of use in association therewith, are provided for use with an endoscopic treatment system. The endoscopic treatment system is preferably of the type described above and in detail in U.S. Pat. No. 8,679,136 and U.S. Pub. No. 2015-0126983; however, other endoscopic treatment systems can also be used.

The endoscopic treatment system preferably includes an endoscope and a distal cap assembly engaged to the endoscope. The endoscope includes a proximal end, a distal end, and first and second instrument channels extending through the endoscope from the proximal to distal ends. The cap assembly is engaged to the distal end of the endoscope.

The cap assembly includes a suturing system comprising a needle holder arm that can be operated at a proximal handle outside the patient via a flexible member extending between proximal and distal ends of the endoscope. The needle holder arm is adapted to releasably hold a needle. Upon operation of the handle, the needle holder arm moves the needle toward a closed position adapted to puncture tissue and toward an opposite open position in which the needle is adapted to be removed from the tissue.

The suture needle system includes a first needle and a second needle. Each of the first and second needles preferably has a substantially common construct. More particularly, each suture needle includes a needle tip member and a needle base member. The needle base member is a tubular construct having first and second axial openings at its respective ends. The needle tip member has a sharpened end which is adapted to pierce tissue and an opposite end provided with a groove which is received into the first axial opening in the needle base member, and a stop that limits insertion of the tip member into the first opening of the base member. Between the opposite end and the groove, the tip member includes a second groove, which aids in engagement and removal of the needle assembly from the needle holder arm. The second axial opening of the base member is adapted to releasably receive the needle holder arm. The tubular wall of the base member includes at least one first laser cut tab that is deformed inwardly into the groove to permanently engage the end of the tip member into an assembled structure. The base member includes an opening in its sidewall, preferably to receive a portion of a suture, and preferably at least one second laser cut tab deformed inwardly into engagement with the received portion of the suture to secure the suture to the needle. The base member includes at least a third laser cut tab that is deformed inwardly to allow removable engagement between the needle and the needle holder arm received into its second axial opening.

The first needle includes an elongate length of suture material sufficient to extend at least the length of the instrument channel. The suture material may be a standard suture material, or may be provided with locking or retention structure along a portion of its length, particularly along a portion near or adjacent the first needle, as described in more detail below.

The second needle includes an opening at which the second needle is longitudinally displaceable over the elongate suture of the first needle. In one embodiment, the opening is provided diametrically through or otherwise through two wall portions of the second needle. In other embodiments, the opening is provided outside of the second needle. The opening may be formed as a loop of suture, in which the two ends of the loop of fixed within or otherwise to the second needle. The opening may be formed as loop of suture in which the loop is formed at one end of a short length of suture and the other end of the short length of suture is fixed within or otherwise to the second needle. The loop may be a loop of fixed dimension, or may be a cinchable or otherwise reducible loop that can be adjusted in size, such as by the application of tension to the suture.

The opening may also be provided with structure adapted to engage with corresponding structure on the elongate suture of the first needle. In embodiments, the elongate suture of the first needle and the loop of the second needle may have one or more retention structures formed to permit the loop to be advanced over the retention structures in a proximal to distal first direction, and which at least inhibits retraction of the loop over the retention structures of the elongate suture in a distal to proximal second direction. The structure along the elongate suture may include, by way of example only, a series of beads, a series of barbs, or an arrangement of teeth. The opening in the suture of second needle may be reducible in diameter to engage the beads or barbs, or include a latch that can engage the beads, barbs, or teeth, all in a manner that inhibits back-off once the loop of the second needle is advanced along the length of the elongate suture or a portion of its length.

The endoscopic treatment system also includes an elongate needle exchange device. The needle exchange device can be positioned within the first instrument channel of the endoscope and has a distal end adapted to deliver a needle to the needle holder arm, and receive and grasp the needle assembly when the needle holder arm is pivoted into the closed position.

The endoscopic treatment system further includes a tissue-grasping instrument. The tissue-grasping instrument can be advanced through the second instrument channel of the endoscope. The tissue-grasping member is adapted, such that when it is advanced to the distal end of the endoscope, it can engage tissue and a portion thereof can be moved relative to the second instrument channel to retract the tissue into the path of a first or second needle engaged by the needle holder arm.

In one method of use, the endoscope and cap assembly are advanced into a patient's gastroesophagheal tract, past the gastroesophagheal junction, and into the stomach. In a method of gastric reduction, the cap assembly is positioned below the fundus and adjacent a lateral portion of the lining of the stomach.

From outside the body, the needle exchange device is loaded with a first needle, and advanced through the first instrument channel. The cap assembly is operated to move the needle holder arm into a closed position, in which the needle moves into alignment with the first instrument channel and engages the needle base member of the first needle advanced to the distal end of the first instrument channel. The first needle is transferred to the needle holder arm, while the elongate suture continues to extend within the first instrument channel. The tissue-grasping instrument is then advanced through the second instrument channel and into engagement with tissue of interest. The tissue-grasping instrument is retracted relative to the second instrument channel to draw the tissue of interest into the path of the first needle. The cap assembly is then operated to move the first needle through the engaged tissue.

The needle exchange device is withdrawn from the first instrument channel. A second needle is loaded into the distal end of the capture device, and the opening of the suture attached to the second needle is advanced over the proximal end of the elongate suture of the first needle and moved down the elongate suture toward its distal end as the needle exchange device is reloaded into the first instrument channel. The needle holder arm is operated to retrieve the second needle from the needle exchange device.

The endoscope with cap assembly is displaced to another location suitable for engaging the stomach lining and which can be used to effect reduction of the stomach. The tissue-grasping instrument is operated to draw tissue into the path of the second needle, and the needle holder arm is operated to move the second needle through the engaged tissue. The needle exchange device is again operated to remove the second needle from the needle holder arm, and then release the second needle.

The process is repeated, with additional second-type needles being advanced over the elongate suture of the first needle and positioned at selected locations in the stomach lining. Preferably, at least for a stomach reduction procedure, the second needles are positions at various locations along the length of the fundus and along anterior, central, and posterior portions of the greater curve of stomach. It is recognized that the elongate suture extends through the openings or loops of a plurality of a second needles displaced about the fundus of the stomach. Once an appropriate engagement of the stomach lining is effected, the elongate suture is tensioned, causing the elongate suture to draw together to the second needles, and the tissue attached thereto. The results in the fundus drawing inward and a reduction in the usable volume of the stomach.

The free end of the elongate suture is then tied or otherwise secured to prevent the openings or loops of the second needles from backing off and releasing the applied tension. Where one or more of the elongate suture or the loop has structure to prevent suture back-off, facilitates holding the applied tension. For example, the loop can be constricted over the elongate suture, or constricted against or mechanically engaged with a retention structure such as barbs or teeth along a portion of the length of the elongate suture to retain an applied tension to the second needles.

While the first and second needles, with their respective sutures, has been described particularly with respect to gastric reduction, it will be appreciated that such system can be used to perform other procedures within the mammalian body.

By way of example, the loop of the second needle can be pre-threaded and guided over the needle exchange device to secure an object such as natural tissue or an implanted device. Such an implanted device can include a stent or tube. The second needle and a portion of the object are pulled through the loop. Then the needle is implanted at a specified location to secure the object in position.

As another example, the second needles can be permanently or temporarily implanted in tissue for at least the purposes of (i) to provide visualization of tissue locations to the surgeon and/or (ii) to position tissue at desired locations.

Other advantages will be appreciated by those skilled in the art in conjunction with the following description.

BRIEF DESCRIPTION OF THE DRAWINGS

Prior Art

Prior Art

Prior Art

Prior Art

Prior Art

Prior Art

Prior Art

Prior Art

Prior Art

Prior Art

Prior Art

Prior Art FIG. 12 through Prior Art FIG. 16 illustrate steps in a surgical suturing procedure using the endoscopic suturing system wherein.

DETAILED DESCRIPTION OF THE PREFERRED EMBODIMENTS

Figure 1:
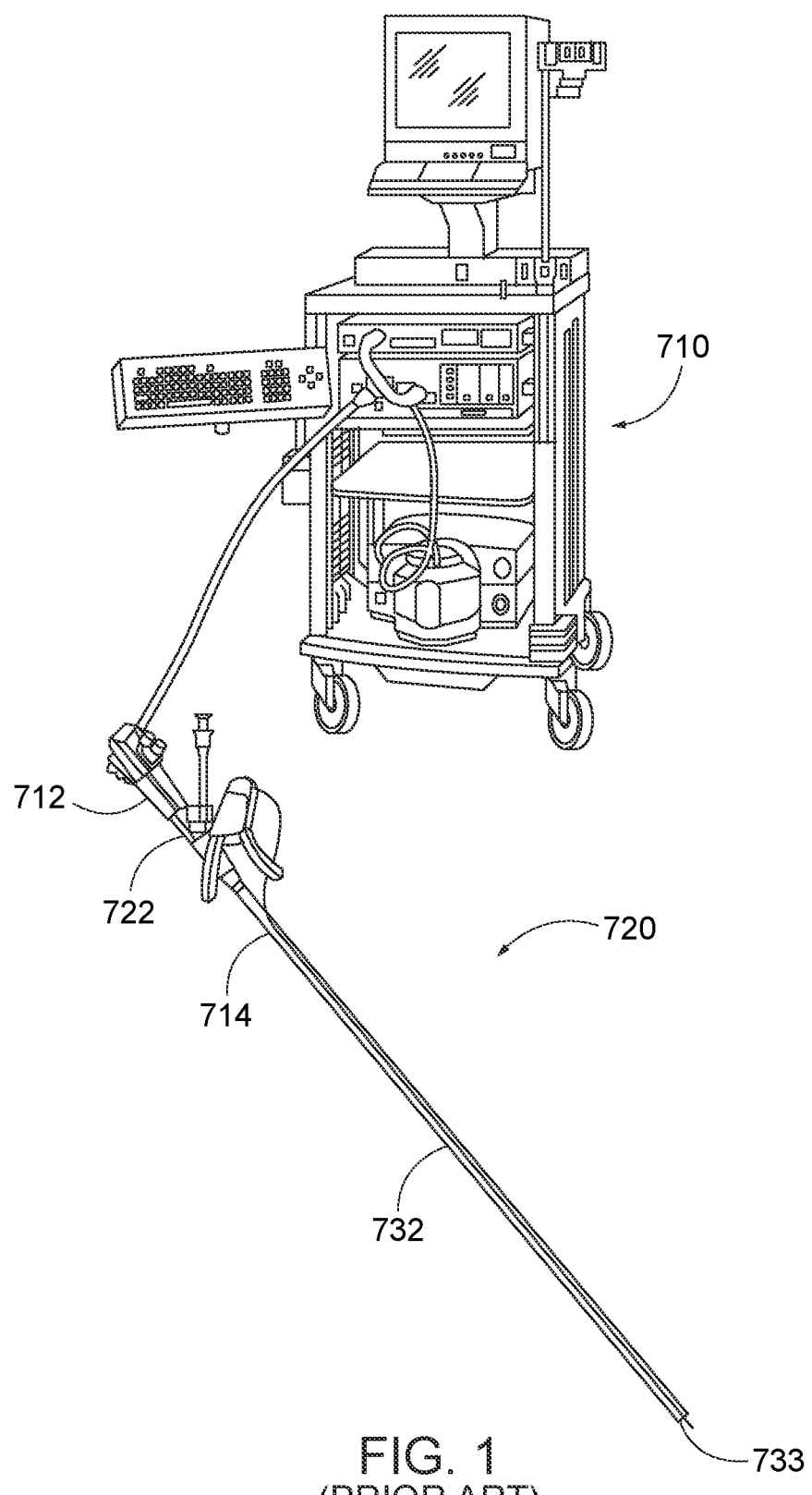
FIG. 1 is an illustrative view showing an endoscopic suturing system with endoscope system.
Figure 2:
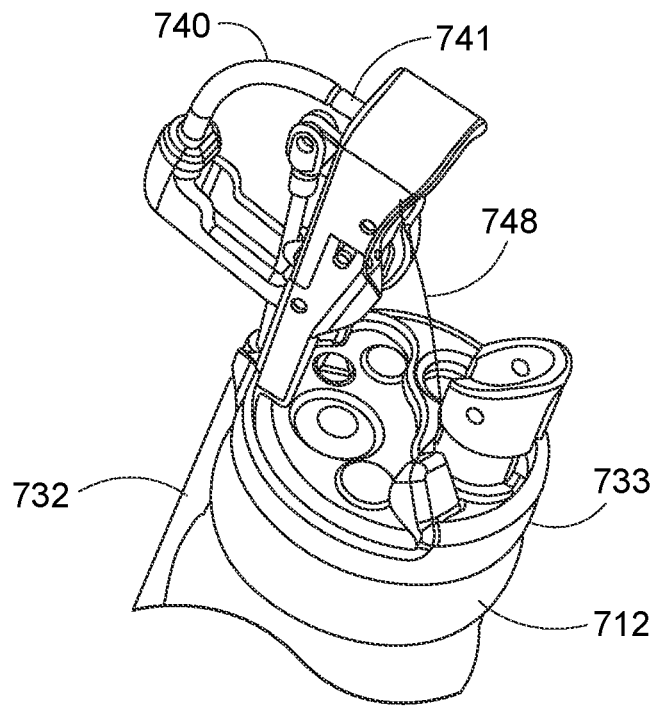
FIG. 2 is an enlarged perspective view of a distal end of an endoscopic suturing system where the needle holder arm of the suturing device is open.
Figure 3:
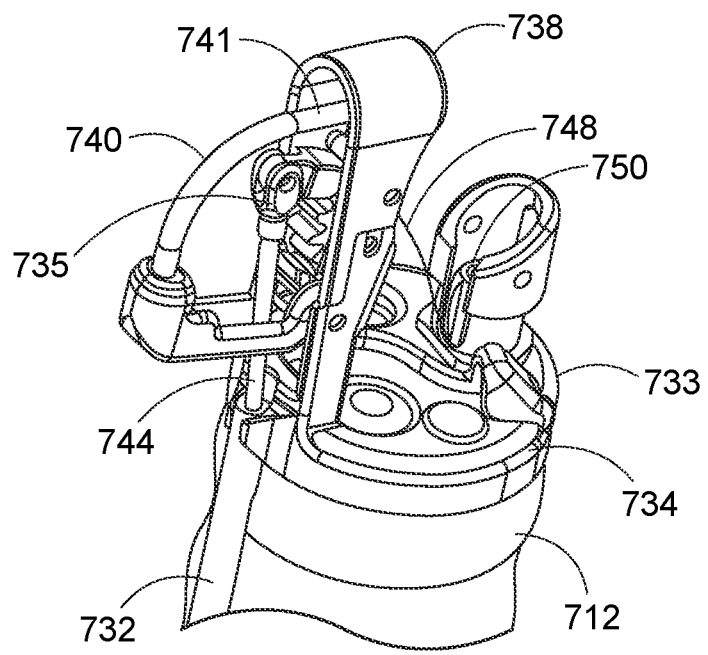
FIG. 3 is an enlarged perspective view of the distal end of the endoscopic suturing system in PRIOR ART FIG. 2 from another viewing angle.
Figure 4:
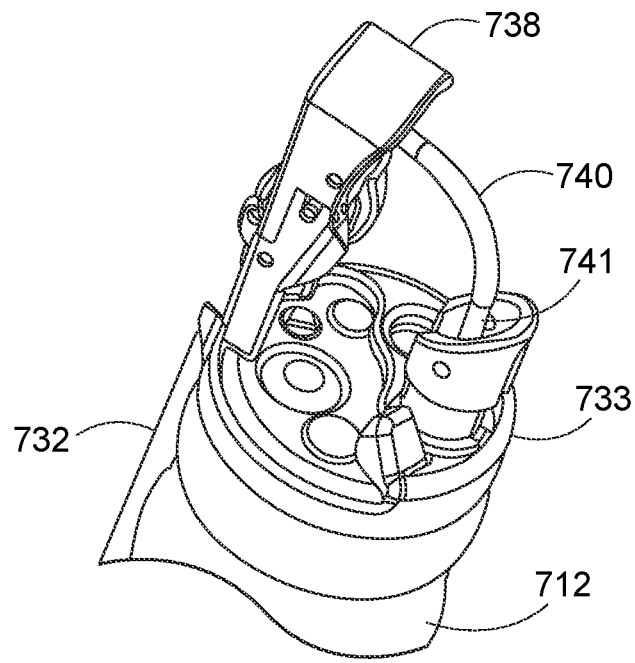
FIG. 4 is an enlarged perspective view of the distal end of an endoscopic suturing system where the needle holder arm of the suturing device is closed.
Figure 5:
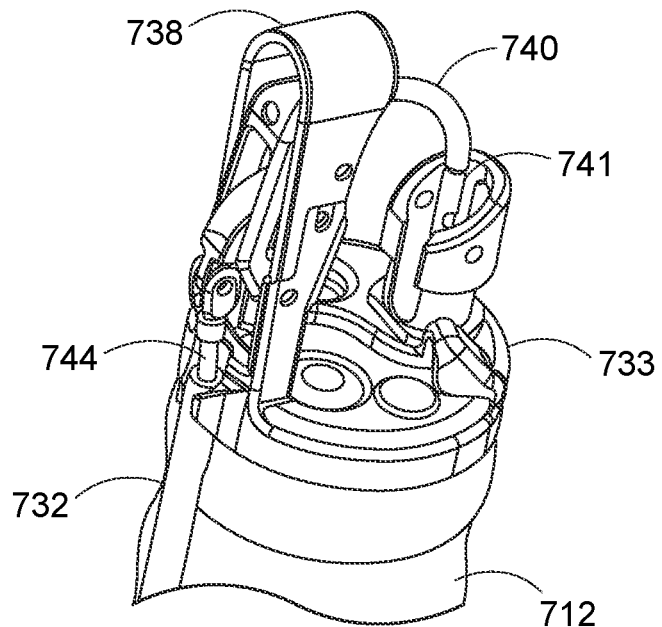
FIG. 5 is an enlarged perspective view of the distal end of the endoscopic suturing system in Prior Art FIG. 4 from another viewing angle.
Figure 6:
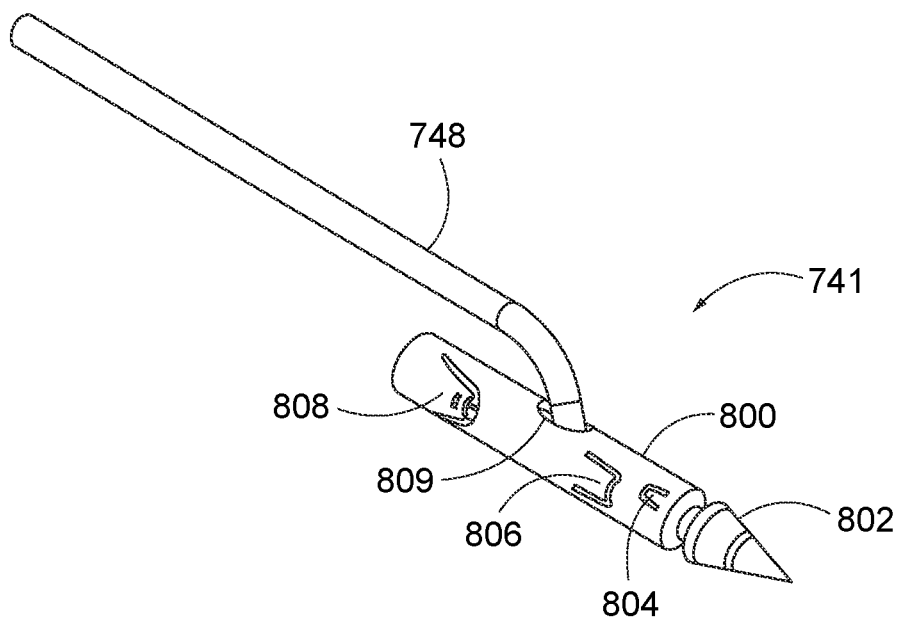
FIG. 6 is an illustrative view of a needle assembly for use with the endoscopic suturing system of Prior Art FIGS. 2 through 5.
Figure 7:
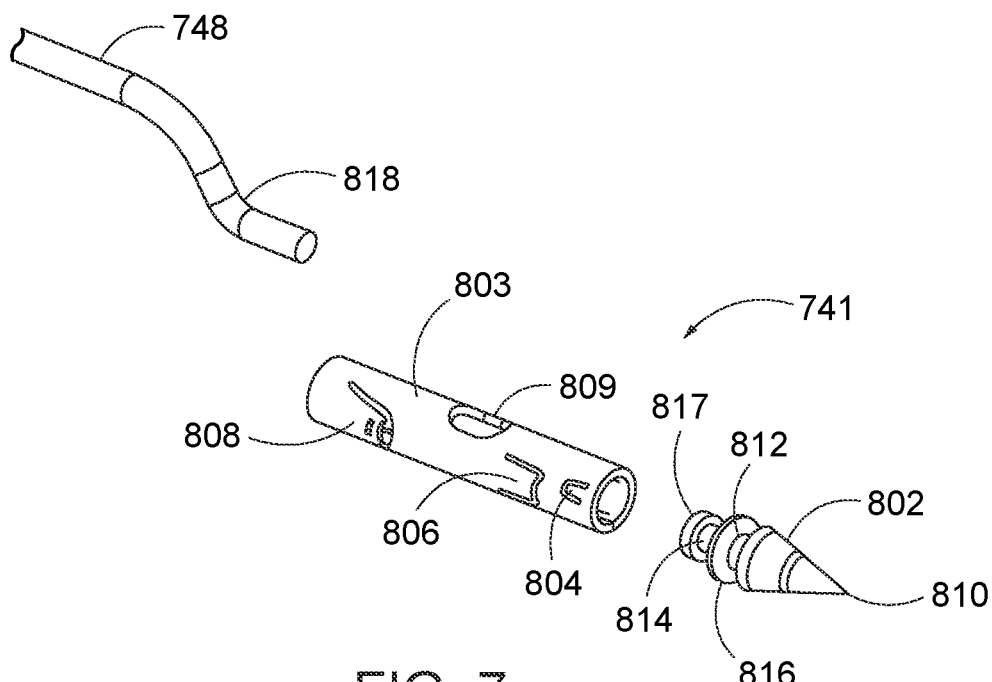
FIG. 7 is an exploded view of the needle assembly of Prior Art FIG. 6.
Figure 8:
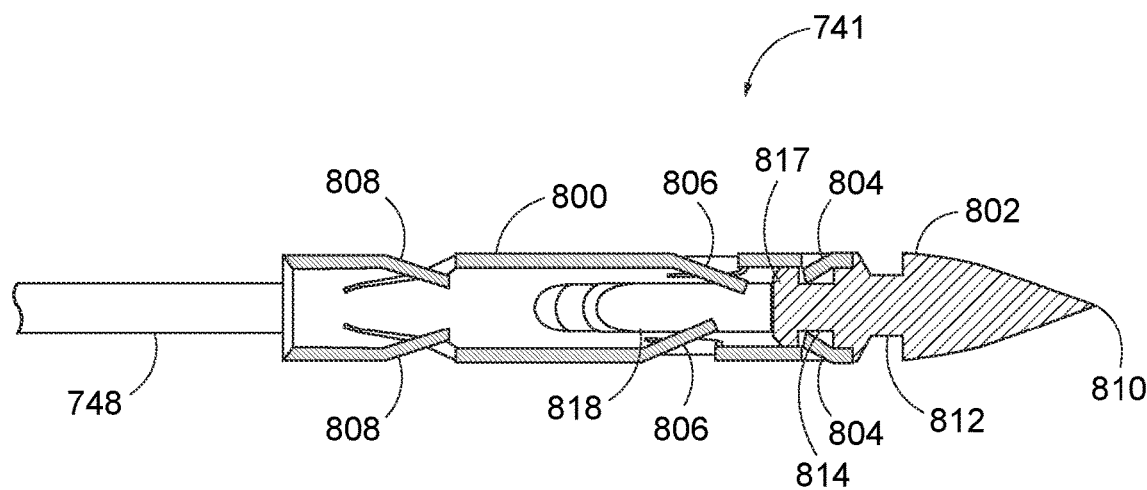
FIG. 8 is a partial section view of a needle assembly for use with the endoscopic suturing system of Prior Art FIGS. 2 through 5.
Figure 9:
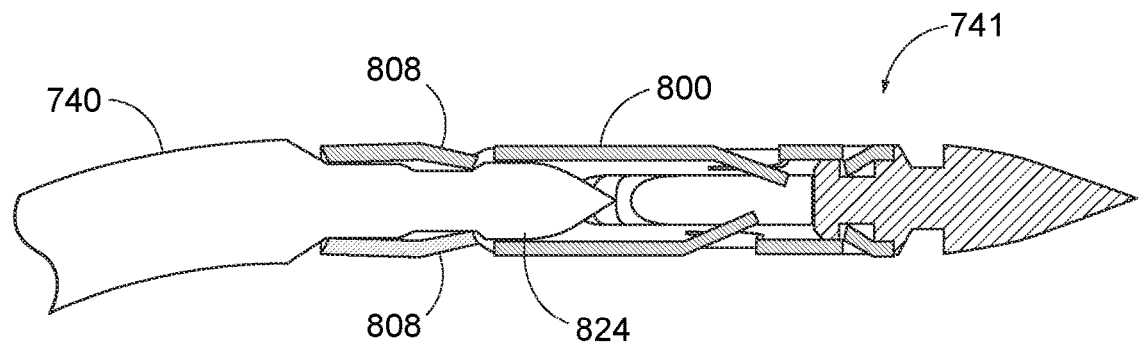
FIG. 9 is a partial section view of the needle assembly engaged with a needle holder arm of the endoscopic suturing system.
Figure 10:
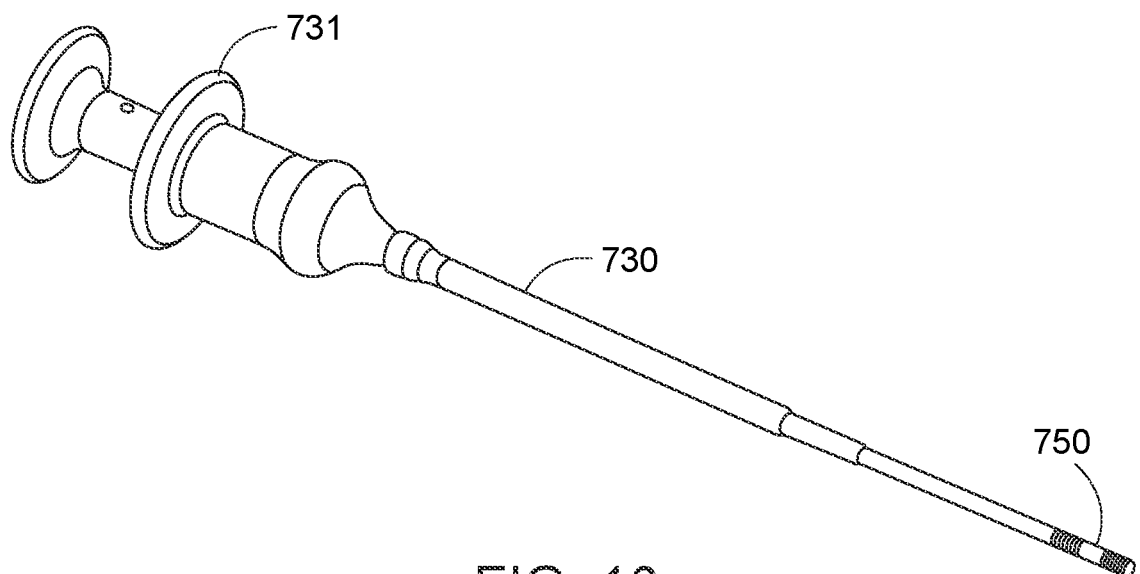
FIG. 10 is a broken perspective view of a needle exchange device for use with the endoscopic suturing system.
Figure 11:
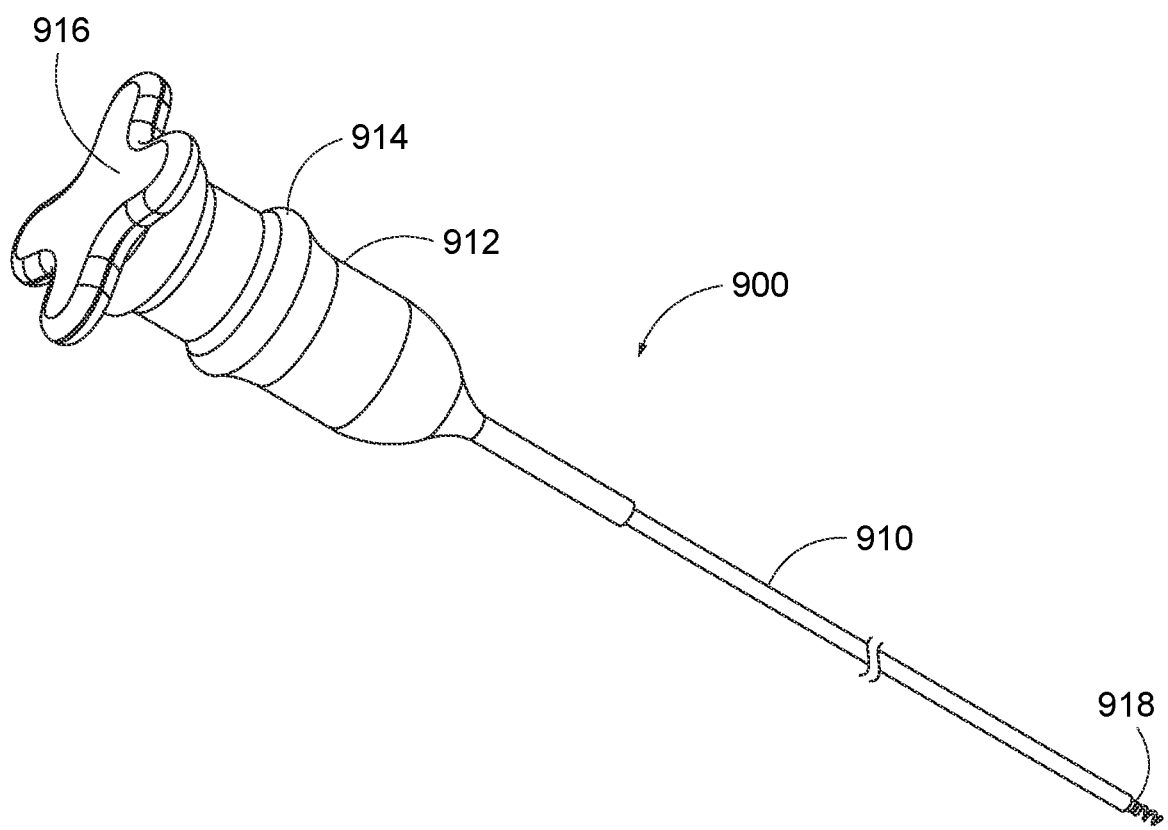
FIG. 11 is a broken perspective view of a tissue-grasping instrument for use with the endoscopic suturing system.
Figure 12:
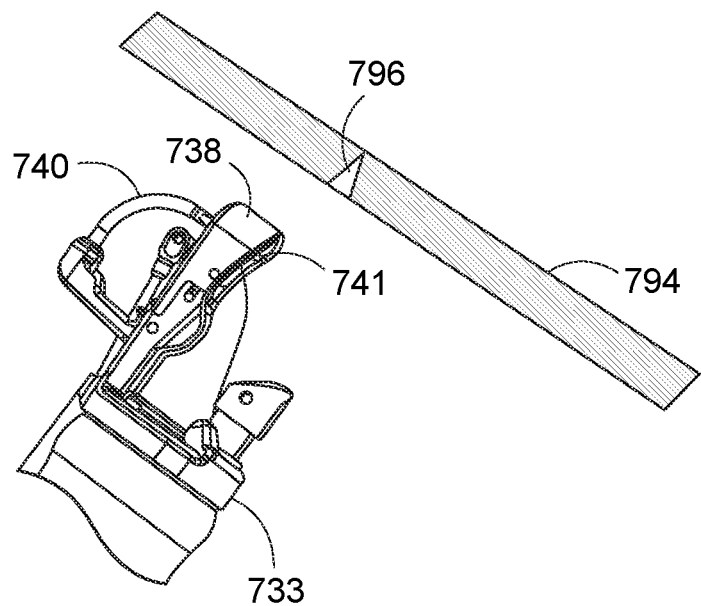
FIG. 12 is a view of a step in which the endoscopic suturing device is positioned adjacent a target treatment location.
Figure 13:
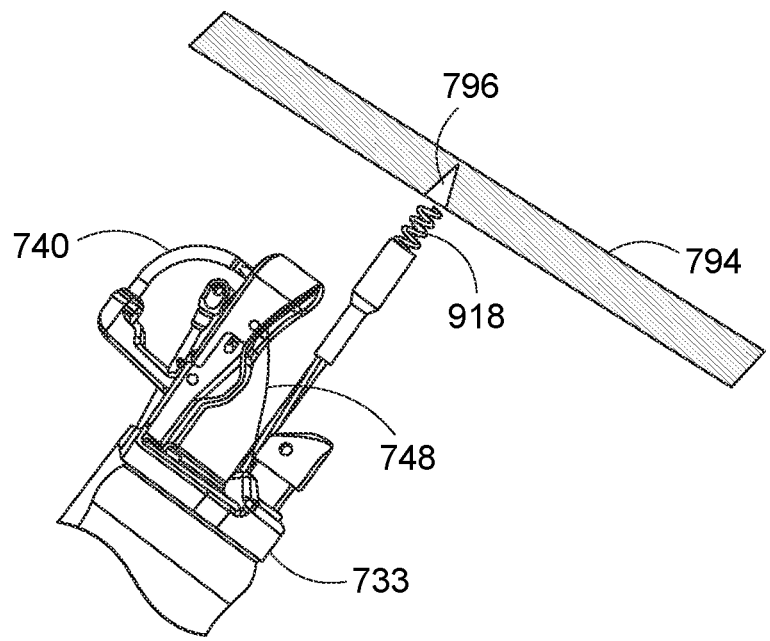
FIG. 13 is a view of a step in which a tissue grasper is extended adjacent the target location.
Figure 14:
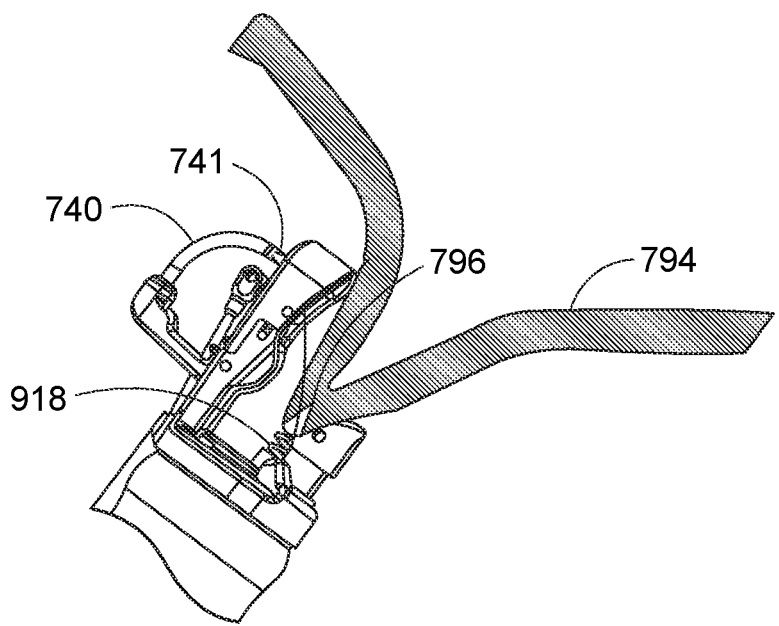
FIG. 14 is a view of a step in which a tissue grasper engages tissue and is substantially retracted to bring tissue in contact with the cap assembly at the end of the endoscope.
Figure 15:
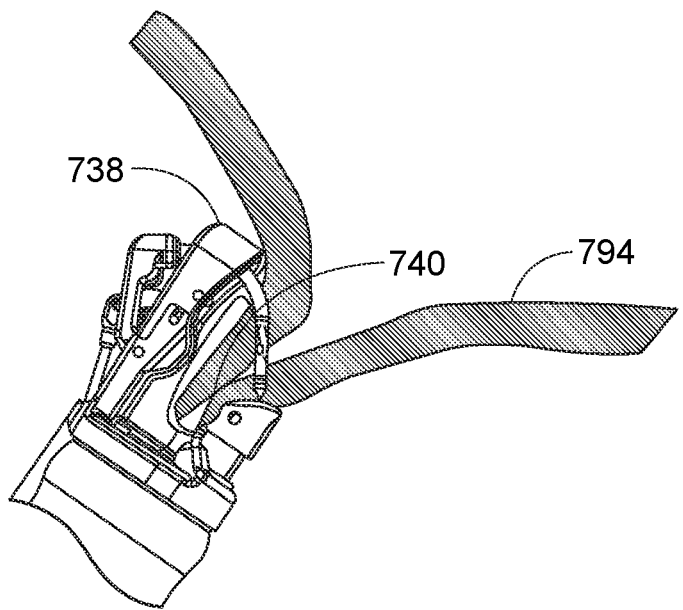
FIG. 15 is a view of a step in which the needle completely pierces tissue.
Figure 16:
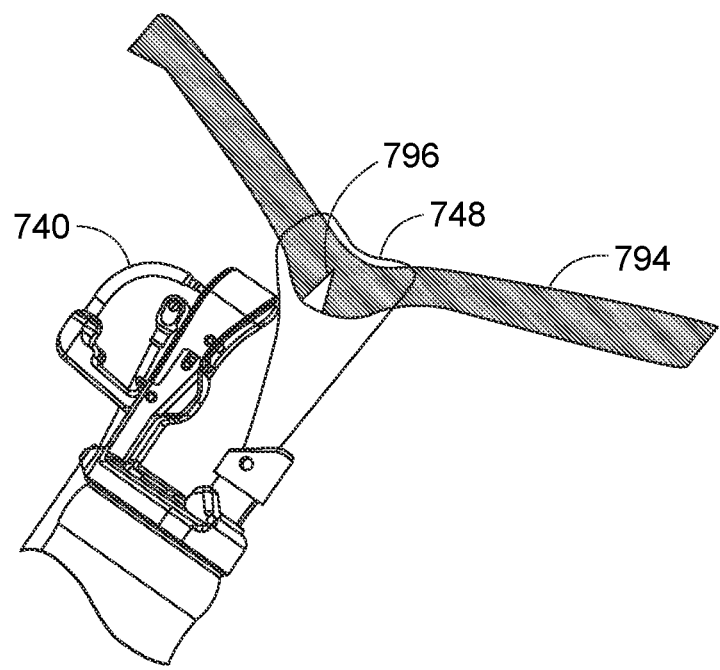
FIG. 16 is a view of a step in which the needle holder arm is removed from the tissue, depositing a suture through the tissue.

With reference to the following description, the terms 'proximal' and 'distal' are defined in reference to the hand of a user of the device, with the term 'proximal' being closer to the user's hand, and the term 'distal' being further from the user's hand such as to often be located further within a body of the patient during use. In addition, the term 'endoscopically', as used herein, means through or with the aid of an endoscope in which the instruments acting to on the body are inserted through a natural orifice, namely the gastroesophageal pathway, preferably without incision to either the dermal or internal tissues of a patient in order to effect for passage of the required instruments. Specifically, it is recognized that suturing does not effect an incision in tissue. In addition, the term 'vertically' as used herein is in reference to the upper and lower portions of the gastrointestinal tract in relation to the passage of nutrients, i.e., with the upper end (fundus) located vertically above the lower end (pylorus) regardless of the orientation of the patient.

In accord the invention, suture needle systems and kits, and methods of use in association therewith, are provided for use with an endoscopic treatment system, and are particularly advantageous in performing an endoscopic gastric reduction. The endoscopic treatment system is preferably of the type described above and in detail in U.S. Pat. No. 8,679,136 and U.S. Pub. No. 2015-0126983, which are hereby incorporated by reference herein in their entireties. However, other endoscopic treatment systems can also be used.

As discussed above with respect to Prior Art FIGS. 1 through 5, a suitable endoscopic treatment system preferably includes an endoscope 712 and a distal cap assembly 733 engaged to the endoscope. The endoscope includes a proximal end, a distal end, and first and second instrument channels extending through the endoscope from the proximal to distal ends. The cap assembly 733 is engaged to the distal end of the endoscope 712. The cap assembly 733 includes a needle holder arm 740 that can be operated at a proximal handle 722 via a flexible member 732 extending between proximal and distal ends of the endoscope. The needle holder arm 740 is adapted to releasably hold one needle at a time. Upon respective operations of the handle, the needle holder arm 740 moves the engaged needle toward a closed position adapted to puncture tissue and then toward an opposite open position in which the needle is adapted to be removed from the tissue.

Figure 17:
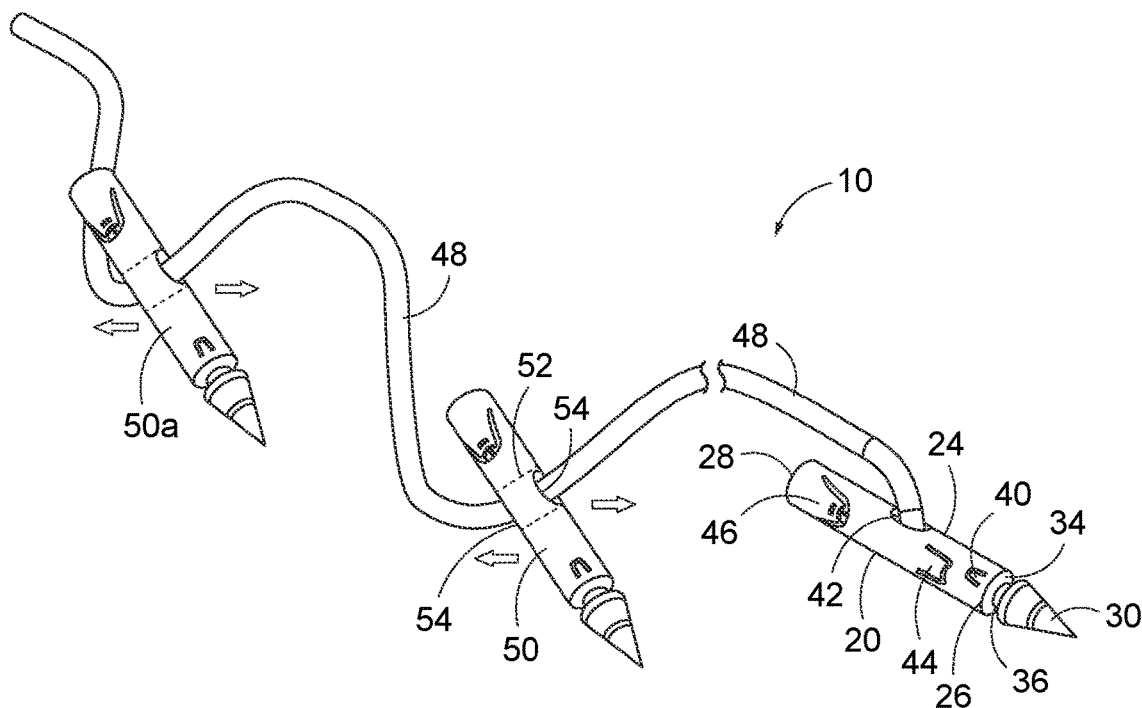
FIG. 17 is a broken perspective view of a first-type needle, and a plurality of sutureless second-type needles advanced onto the suture of the first-type needle.

Turning now to FIG. 17, an embodiment of the suture needle system 10 for use with an endoscopic treatment system includes a first needle 20 and a second needle 50. For engagement with the needle holder 740 of the suturing instrument at the end of the endoscope 712, each of the first and second needles 20, 50 is preferably straight and extends along a respective axis. Each of the first and second needles 20, 50 preferably also has a substantially common construct.

More particularly, and shown with respect to first needle 20, each suture needle includes a needle tip member 22 and a needle base member 24. The needle base member 24 is a tubular construct having first and second axial openings 26, 28 at its respective ends. The needle tip member 22 has a sharpened end 30 which is adapted to pierce tissue and an opposite end 32 provided with a first groove (not shown)

which is received into the first axial opening 26 in the needle base member, and a stop 34 that limits insertion of the tip member into the first opening of the base member. Between the sharpened end 32 and the first groove, the tip member includes a second groove 36, which aids in engagement and removal of the needle assembly from the needle holder arm. The second axial opening 38 of the base member is adapted to receive the needle holder arm 740 of the cap assembly 733, as discussed further below. The tubular wall of the base member includes at least one first laser cut tab 40 that is deformed inwardly into the first groove to permanently engage the end of the tip member 22 into an assembled structure with the base member 24. The base member 24 includes an opening 42 in its sidewall, preferably to receive a portion of a suture 48, and preferably at least one second laser cut tab 44 from the tubular wall is deformed inwardly into engagement with the received portion of the suture 48 to secure the suture to the needle. The base member 24 includes at least a third laser cut tab 46 that is deformed inwardly to allow removable engagement between the needle assembly 10 and the needle holder arm received into its second axial opening 28.

The suture 48 of the first needle 20 may be an elongate strand, multi-strand, strip, or braid of any suitable material. By way of example, the suture 48 may be made of polymeric and/or metal filaments, or elastic or inelastic materials. The suture 48 is of sufficient length to extend the length of the instrument channel of the endoscope and beyond to a target tissue site.

The second needle 50 has a construction substantially similar to the first needle, unless differences are specifically noted herein. The second needle 50 is provided with a suture passage opening 52 extending transversely to (and more preferably diametrically through) the sidewall. The suture passage opening is defined by two apertures 54 in the sidewall of the base member of the second needle. The apertures 54 may be fully defined holes in the sidewalls or defined by laser cut tabs displaced relative to the sidewall. The apertures 54 are preferably in opposing sidewalls. Alternatively, the apertures can be longitudinally displaced in opposing sidewalls, or as two apertures in a common side of the wall of the second needle. Regardless, the proximal end of suture 48 can be passed into one aperture and out of the other aperture. The second needle 50 then can be advanced distally over the suture 48 of the first needle 20 at the opening in the second needle. As noted with respect to another second needle 50a, multiple second-type needles (only two shown by way of example) can be advanced onto the elongate suture 48 of the first needle. The spacing of the second needles 50, 50a relative to each other and along the elongate suture 48 can be adjusted such that each of the first 20 and second needles 50, 50a can be directed into respective target tissue, as discussed below. Then, if the apertures in the second needles include tabs or other retention structure, such tabs can be deformed onto the elongate suture to fix the spacing of the second needles relative to the first needle.

Figure 18:
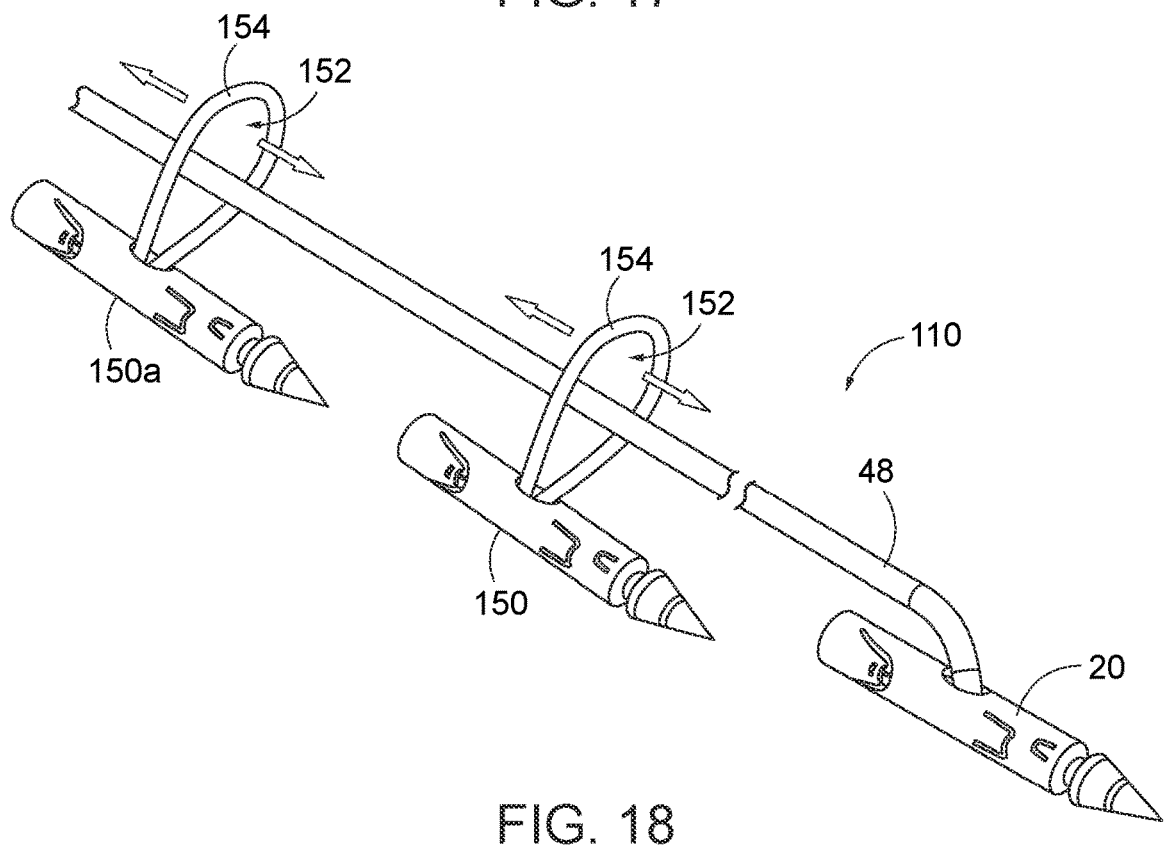
FIG. 18 is a broken perspective view of a first-type needle, and a plurality of second-type needles, each with suture loop, advanced onto the suture of the first-type needle.

Referring to FIG. 18, in another embodiment of the needle system 110, the sidewall of the needle does not necessarily form the opening for the elongate suture. Rather, the opening 152 provided to the second needle 150 is defined outside the second needle by a short loop 154 of suture, in which the two ends of a short loop 154 of suture fixed in the suture aperture 156 of the second needle. The short loop 154 of suture can be made of any suitable material. Such materials can include conventional or non-conventional suture materials, threaded-like materials, elastic or inelastic materials, any plastic or synthetic materials, any metal materials, bioabsorbable materials, non-absorbable materials, monofilaments, multifilaments, and braids. The material and/or dimensions and/or appearance of the short loop 154 can be the same or different than the material comprising the elongate suture 48 of the first needle 20. The short loop diameter in various embodiments has a diameter that does not exceed the length of the needle. Such a relatively small diameter is advantageous in relation to the gastric reduction method described below. Nevertheless, other relationships between the needle length and loop diameter can be put into effect. The second needle 150 is longitudinally displaceable over the elongate suture 48 of the first needle 20 at the opening 152. A plurality of second needles 150, 150a, each with like or respectively-formed short loop portions 154, can similarly be advanced over the elongate suture 48 of the first needle, preferably in a proximal to distal direction. This can be particularly advantageous, as set forth with respect to methods described below.

Figure 19:
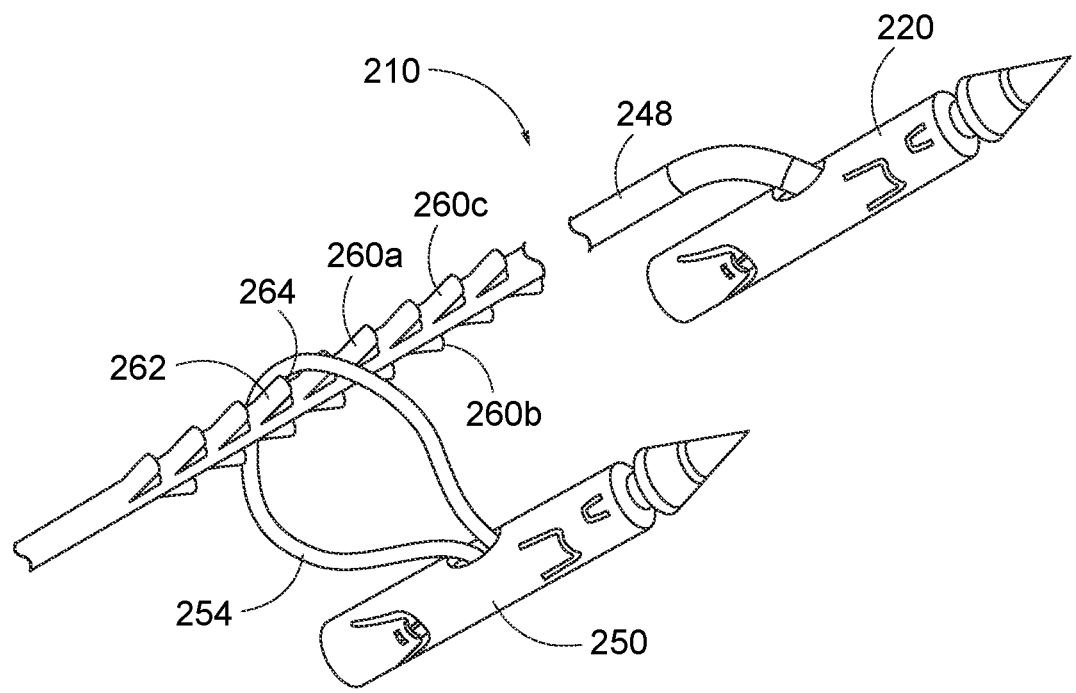
FIG. 19 is a broken perspective view of another embodiment of a first-type needle, and a plurality of the second-type needles, each with suture loop, advanced onto the suture of the first-type needle.

Turning now to FIG. 19, another embodiment of a needle system 210 is shown. The needle system includes a first needle 220 with elongate suture 248, and at least one second needle 250 with suture loop 254. In accord with the embodiment, the elongate suture includes structure that is adapted to permit distal displacement of the suture loop thereover, but resists relatively proximal displacement of the suture loop relative to the structure. The structure is provided along at least a portion of the suture length. In the embodiment shown, the structure is a linear arrangement of barbs 260a, 260b, 260c, . . . that alternate on laterally opposite sides of the suture. The barbs define a proximal ramp wall 262 that the suture loop can be guided thereover, and a distal catch surface 264 that traps the suture loop 254 when the suture loop is drawn into contact with such catch. The structure provides, facilitates, or enhances engagement between the first and second needles 220, 250 at their respective sutures.

Figure 20:
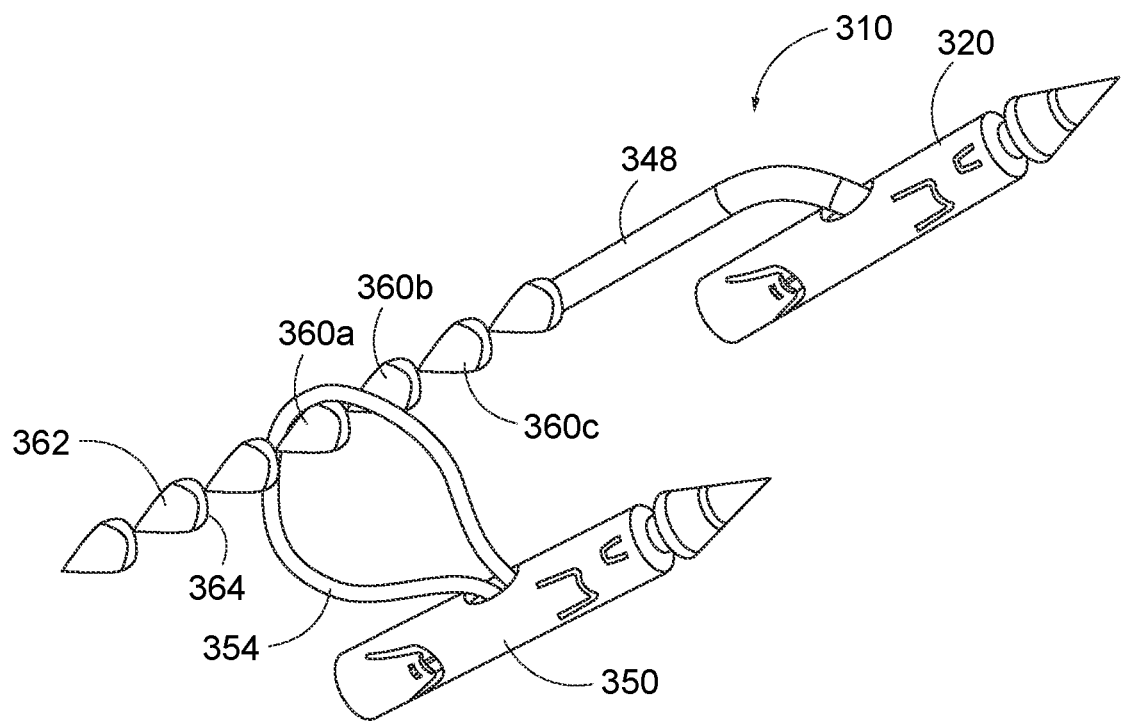
FIG. 20 is a broken perspective view of a further embodiment of a first-type needle, and a plurality of the second-type needles, each with suture loop, advanced onto the suture of the first-type needle.

Referring to FIG. 20, another embodiment of a needle system 310, with needles 320 and 350, is shown. Needle 320 includes an elongate suture 348 with another barbed structure to facilitate engagement and retention between the first and second needles and their respective sutures. More particularly, the barbs 360a, 360b, 360c, . . . are provided as connected conical elements. The barbs each have a proximal conical wall 362 that functions as a ramp, and a distal catch surface 364.

Figure 21:
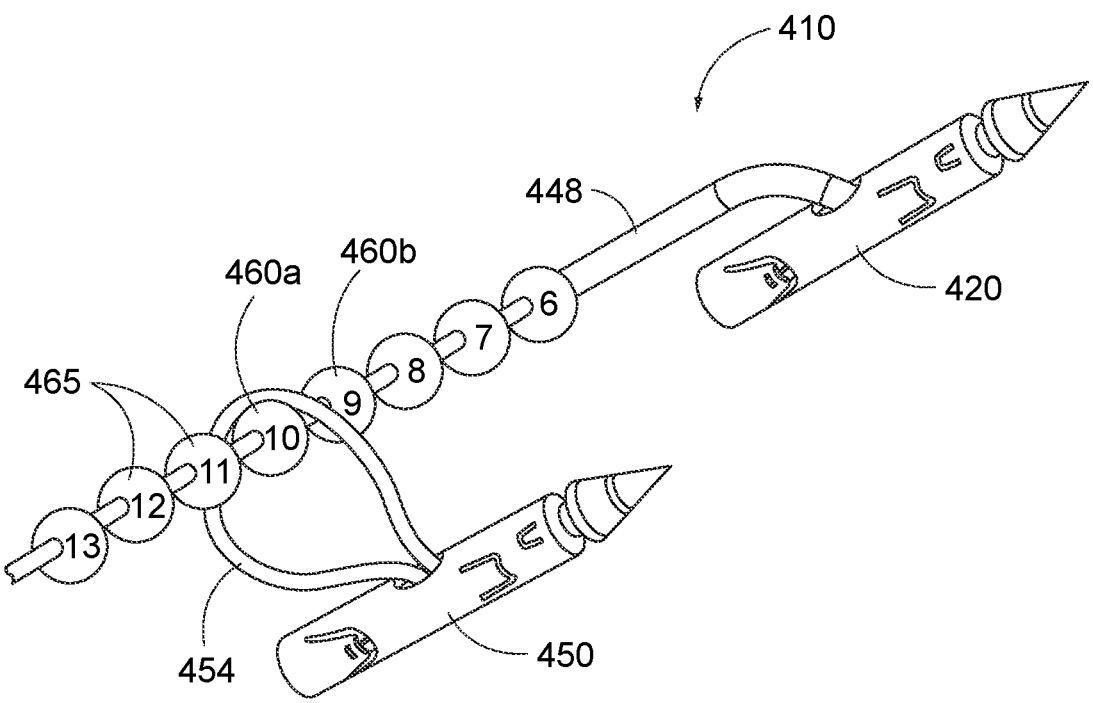
FIG. 21 is a broken perspective view of another embodiment of a first-type needle, and a plurality of the second-type needles, each with suture loop, advanced onto the suture of the first-type needle.

Referring to FIG. 21, another embodiment of a needle system 410, with needles 420 and 450, is shown. Needle 420 includes an elongate suture 448 with a serial arrangement of beads 460a, 460b, . . . adapted to facilitate engagement and retention between the first and second needles at their respective sutures 448, 454.

In each of the elongate sutures provided with retention structure, e.g., barbs or beads, the retention structure may be provided with indicia 465 to indicate distances along the elongate suture relative to the needle 230, 330, 430. The indicia may be in the form of number markings (as shown), or colors, or patterns on the longitudinally displaced structures. In addition, elongate sutures without retention structure may also be provided with similar distance indicia marked on the suture, including graphical indicia or a change in suture color at determined intervals, e.g., each 2 cm.

Figure 22:
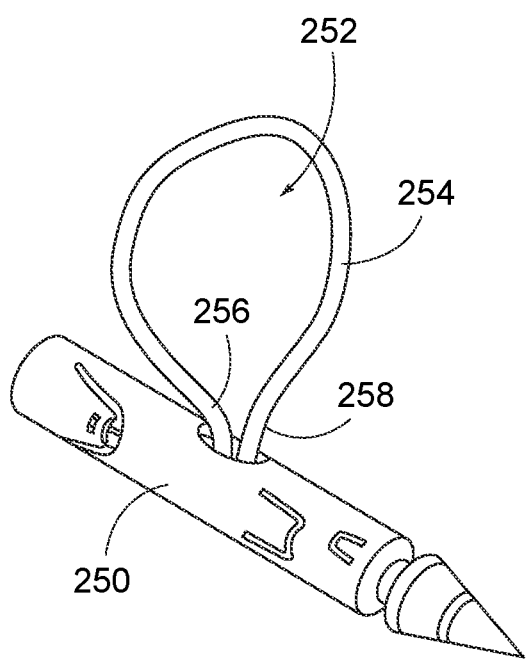
FIG. 22 is a perspective view of an embodiment of the second-type needle with suture loop.
Figure 23:
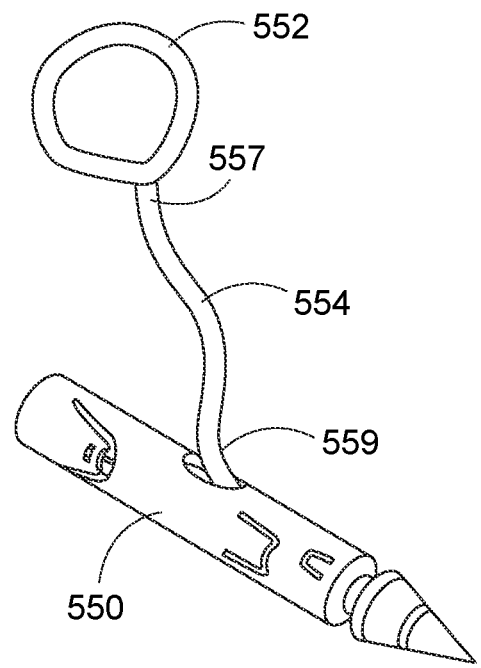
FIG. 23 is a perspective view of another embodiment of the second-type needle with a loop.

The opening 252 in suture 254 has been shown being defined by the two ends 256, 258 of the suture 254 (FIG. 22). However, the opening can alternatively be formed as a loop 552 positioned at one end 557 of a short length 554 of suture, whereas the other end 559 of the short length of suture is fixed within the second needle 550 (FIG. 23). As shown in FIG. 23, the loop 552 can be fixed in dimension. Such fixed dimension loop 552 can be formed by a knotted end of the flexible suture 554, a rigid eyelet at the end of the suture or fusing a loop onto the end of the suture.

Figure 24:
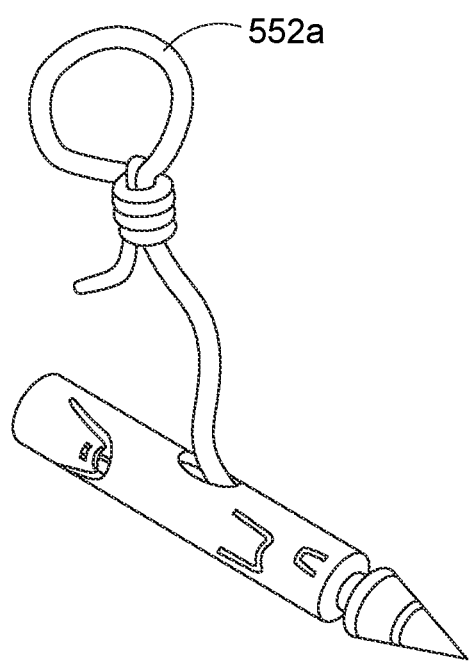
FIG. 24 is a perspective view of yet another embodiment of the second-type needle with a cinchable loop.

Alternatively, referring to FIG. 24, the loop 552a may be adjustable in size, so that the opening can be constricted against the first suture 548. An adjustable loop 552a can be formed by a cinchable portion of suture or a self-tightening coil. An adjustable loop allows the loop 552a to be tightened and closed on the elongate suture of the first needle between the barbed or beaded retaining structure shown in FIGS. 19-21. The adjustable loop permits temporarily stabilizing the second needle relative the first needle to assess progress of a tissue manipulation and suturing procedure, and/or retention until the adjustable loop is further reduced to be permanently secured relative to a fixed location along the elongate suture, and/or retention of the second needle until a permanent cinch is positioned on the elongate suture to fix the position of the second needle relative to the first needle.

Figure 25:
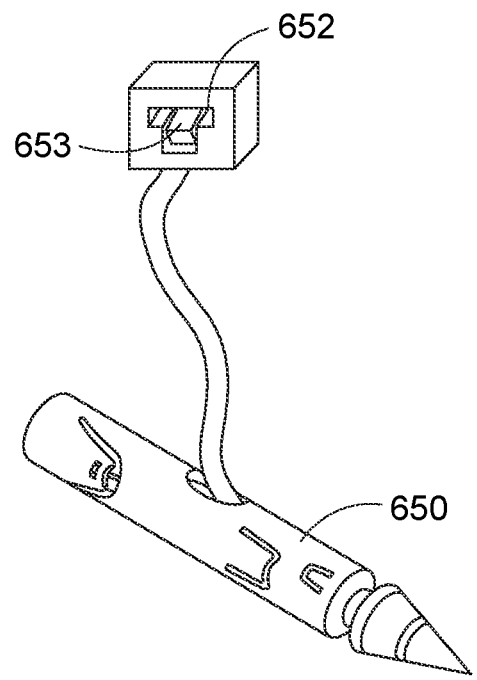
FIG. 25 is a perspective view of a further embodiment of the second-type needle with a latching mechanism.
Figure 26:
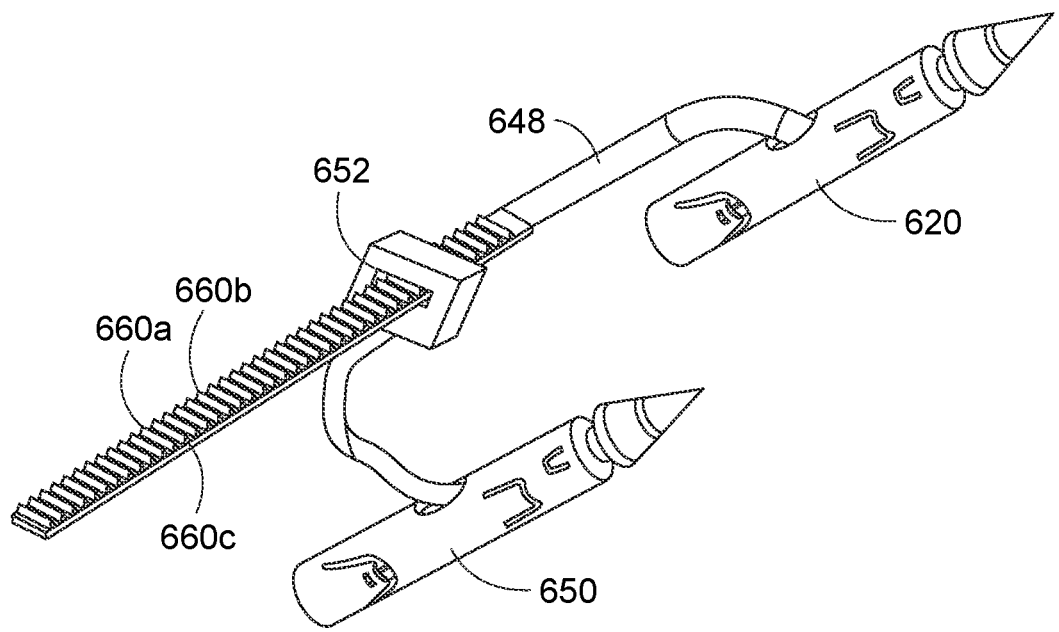
FIG. 26 is a perspective view of another embodiment of a first-type needle having an elongate suture, and a second-type needle with latching structure to engage corresponding structure on the elongate suture.

Turning now to FIGS. 25 and 26, an embodiment of a second needle 650 includes a fixed opening adapted to mechanically cooperate with retaining structure along the elongate suture 648 of the first needle 620. The elongate suture 648 includes a series of teeth 660a, 660b, 660c, . . . such as formed on a zip tie. The opening for the second needle 650 includes a latch 652 sized to receive therethrough the elongate suture 648. The latch 652 includes a resiliently deformable fastener 653 that is adapted to permit ratcheting advancement of the teeth 660a, 660b, 660c, . . . through the latch in one direction and prevent retraction of the teeth against the fastener 653 and through the latch 652 in an opposition direction. With such structure, the second needle 620 can be advanced over the elongate suture 648 and toward the first needle 620 and retained at a minimum distance relative thereto. Additionally, the locking mechanism provides the same or similar advantage to that described above with respect to the adjustable loops.

In an exemplar method of using embodiments of the needle system described herein, the first needle and a plurality of second needles are used together in a gastric reduction procedure. In such procedure, the capacity of the stomach is reduced to limit the patient's desired caloric intake and thereby result in sustained weight loss over time.

Figure 27A:
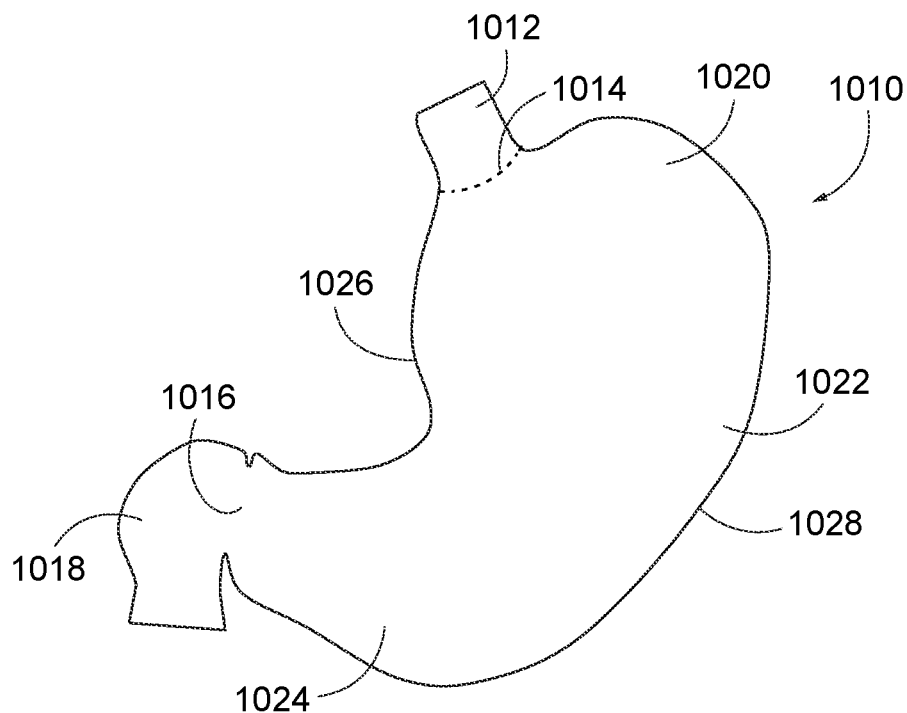
FIG. 27A through 48 illustrate a method of gastric reduction according to an invention herein.

Referring to FIG. 27A, an illustration of the stomach 1010 with standard reference locations are shown. The gastroesophagheal junction 1014 located at the upper end of the stomach 1010 is joined to the lower end of the esophagus 1012, and the pylorus 1016 defined at the lower end of the stomach is joined to the duodendum 1018 of the small intestines. The upper portion of the stomach is the fundus 1020 and extends vertically above of the gastroesophagheal junction 1014, the central portion is the body 1022, and the lower portion of the stomach is the antrum 1024. The medial side of the stomach forms a concave curve referred to as the lesser curvature (or curve) 1026, whereas the lateral side of the stomach forms a larger convex curve referred to as the greater curvature (or curve) 1028.

Figure 27B:
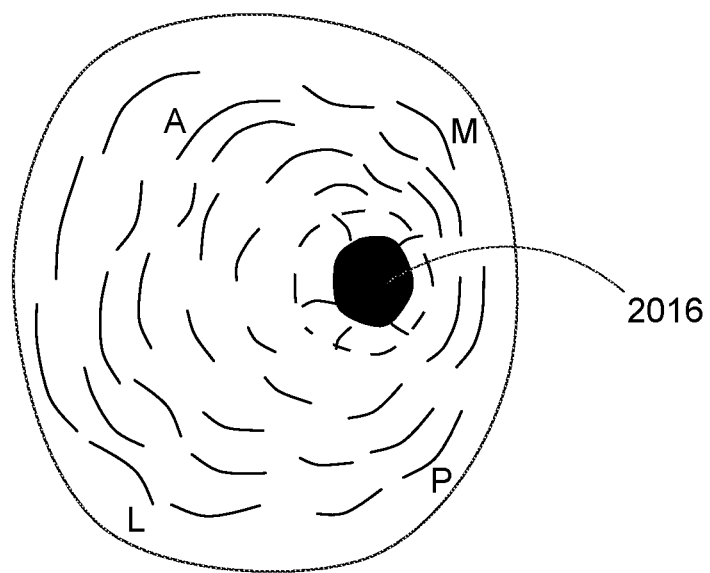

Turning now to FIG. 27B, an interior of the stomach 1010 is shown, viewed from the fundus 1020 (top) toward the pylorus 1016 (bottom). In addition, the anterior (A), posterior (P), lateral (L), and medial (M) sides of the stomach are identified. The lateral side (L) extends with the greater curvature 1028 of the stomach 1010, and the opposing medial side (M) extends with the lesser curvature 1026 (see FIG. 27A).

Figure 28A:
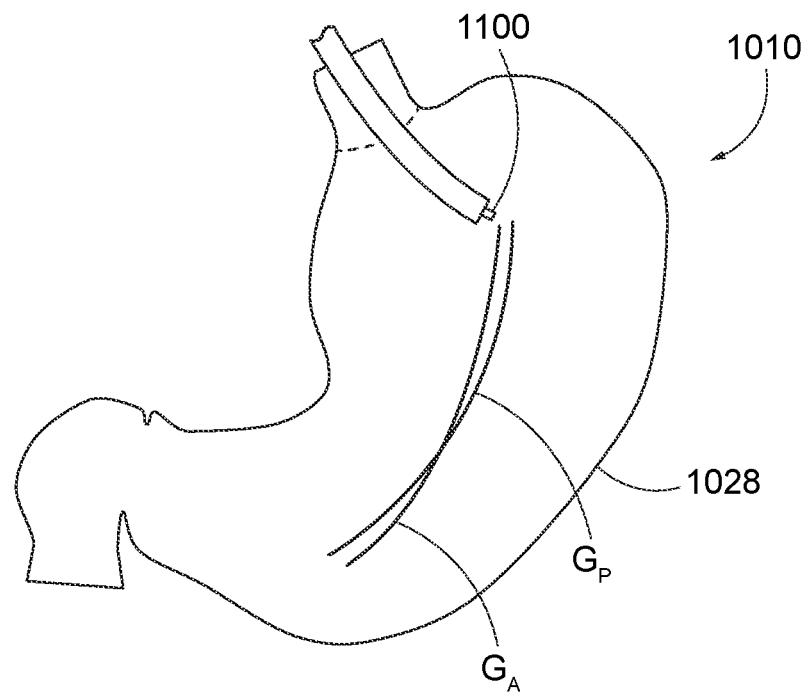
Figure 28B:
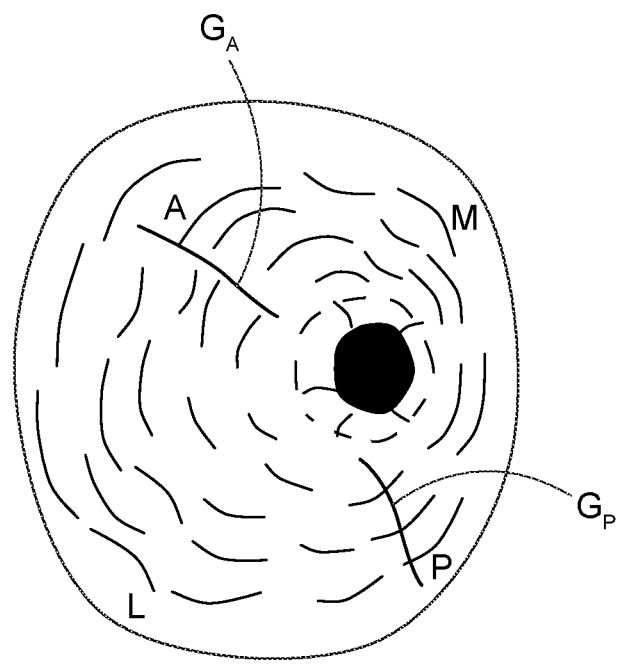

Referring to FIGS. 28A and 28B, one or more guidelines $G_A$, $G_P$ can be marked along, for example, the anterior and posterior sides A, P of the stomach 1010 at the greater curvature 1028 to enhance visualization of the appropriate location of initial and subsequent suture fixation. The guidelines may be marked with a coagulator, dye or other marking device or substance. One preferred marking device is the argon plasma coagulator 1100, which can be used to create a continuous guideline on the stomach lining. Another device that can be used is a needle knife and dye, which can generate dotted-line or continuous guidelines. The stitching pattern subsequently proceeds along and/or relative to the guidelines $G_A$, $G_P$. The guidelines, while preferred, are not essential to the practice of the method.

After marking the guidelines, the first needle 20 is preferably placed at a distalmost location for the procedure (in the antrum 1024, and preferably adjacent the pylorus 1016). Subsequently, second needles are placed at one or more of (i) proximally-displaced locations relative to the first needle, (ii) vertically-displaced locations relative to the first needle, (iii) at different sides of the stomach relative to the first needle, and (iv) helically-displaced locations relative to the first needle. Further, as discussed above, the second needles are each provided with an opening (various embodiments discussed above) at which the second needle can be advanced over the elongate suture of the first needle.

Figure 29:
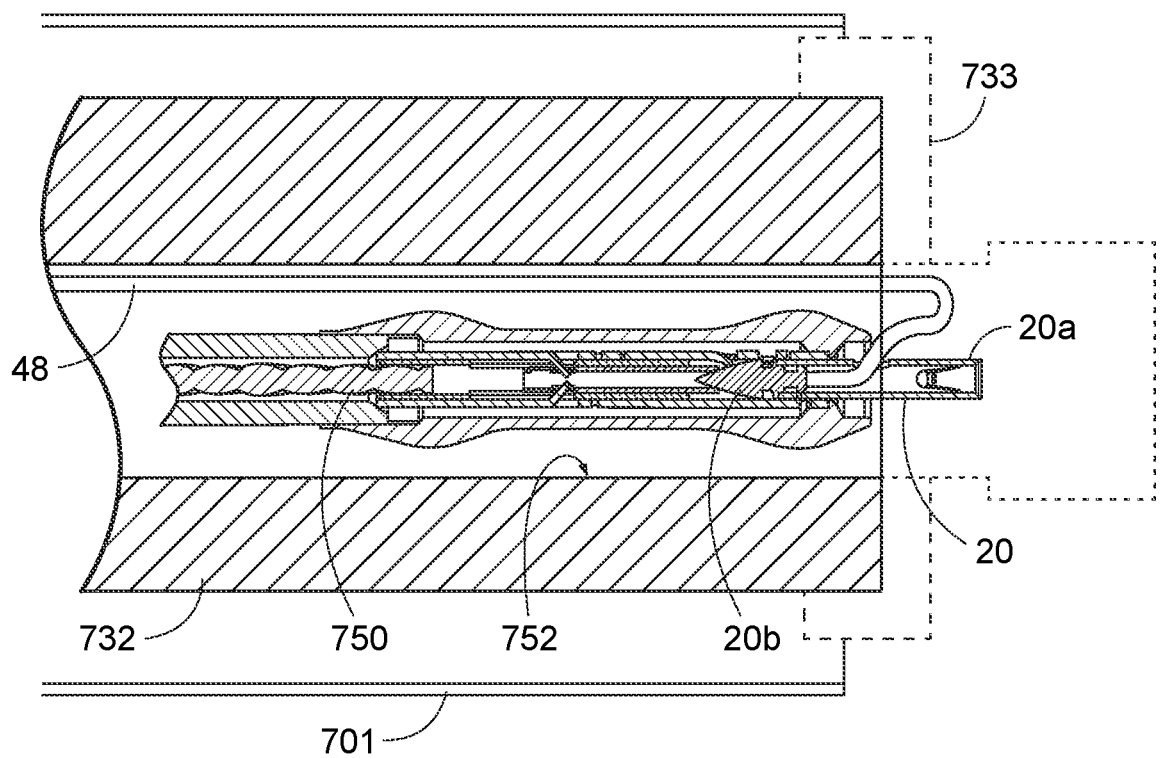

Turning now to FIG. 29, as one of the initial steps in the procedure, an endoscope 732 is provided with a cap assembly 733 including a needle holder arm 740 that is operable from outside the body of the patient. Such endoscope and cap assembly are as described briefly above and described in detail in U.S. Pat. No. 8,679,136 to Mitelberg, which is hereby incorporated by reference herein in its entirety. The endoscope 712 and cap assembly 733 are advanced into a patient's gastroesophagheal tract, past the gastroesophagheal junction, and into the stomach. The endoscope and cap assembly may be advanced through a flexible port 701 to facilitate insertion of the instrument through the patient's esophagus and reduce irritation to the patient. In a method of gastric reduction, the cap assembly 733 is positioned below the fundus and adjacent a lateral portion of the lining of the stomach.

Figure 30:
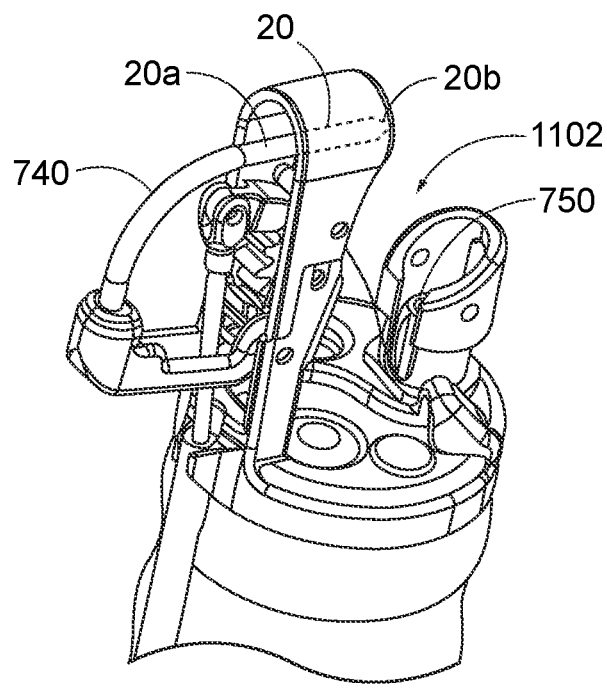
Figure 31:
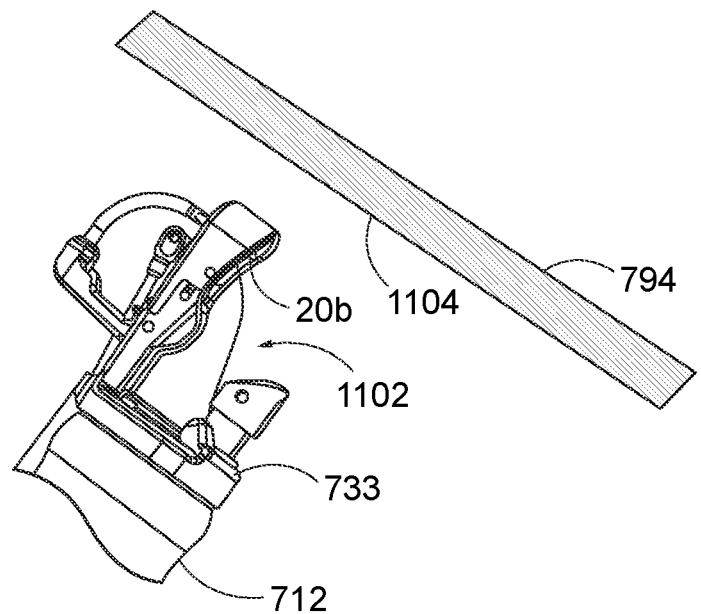
Figure 32:
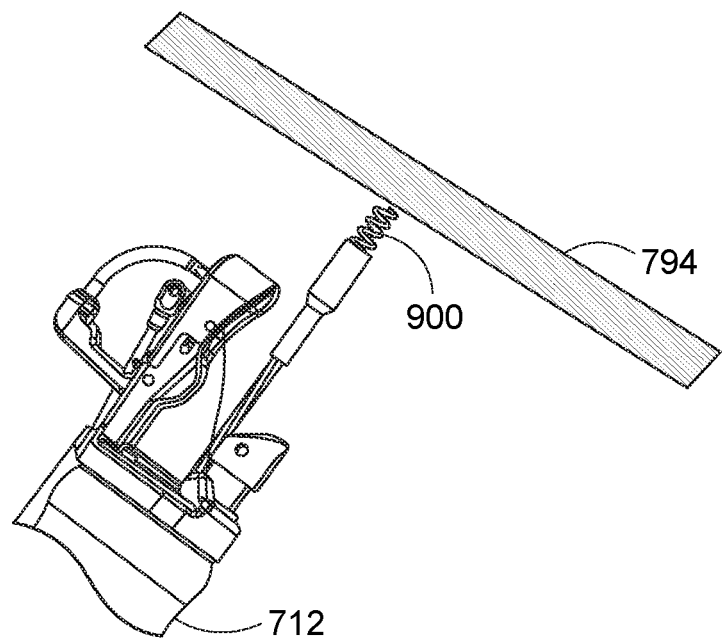

In addition, from outside the body, a needle exchange device 750, as described briefly above and in detail in previously incorporated U.S. Pat. No. 8,679,136 to Mitelberg, is loaded with the first needle 20 described herein, and advanced through a first instrument channel 752 of the endoscope 732, leaving its elongate suture 48 co-extending within the first instrument channel alongside the needle exchange device. This step may occur either before or after the endoscope has been advanced into the patient. With the cap assembly 733 in the stomach of the patient, and the needle exchange device 750 extending within the first instrument channel 752, the cap assembly 733 is then operated to close the needle holder arm 740 against the cooperating free end 20a of the first needle 20 until the arm and first needle are mechanically or frictionally engaged together. The needle exchange device 750 is then operated to release the first needle 20 from the distal end of the exchange device. The needle holder arm 740 is then opened to swing the sharp piercing tip 20b of the first needle out of the first instrument channel 752 and away from a distal end cap of the cap assembly and a distal end of the endoscope (to the positions shown in FIGS. 30 and 31), thereby providing a space 1102 between the piercing tip 20b of the first needle and the distal end cap of the cap assembly 733. The endoscope 732 is maneuvered to orient the distal end cap assembly 733 to a tissue location 1104 below the fundus, e.g., at or adjacent the antrum or even near the pylorus.

Figure 33:
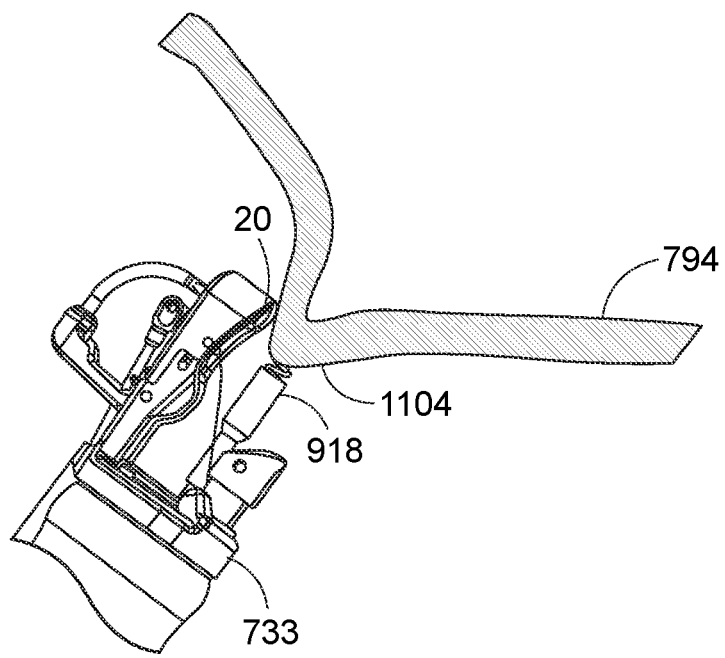
Figure 34:
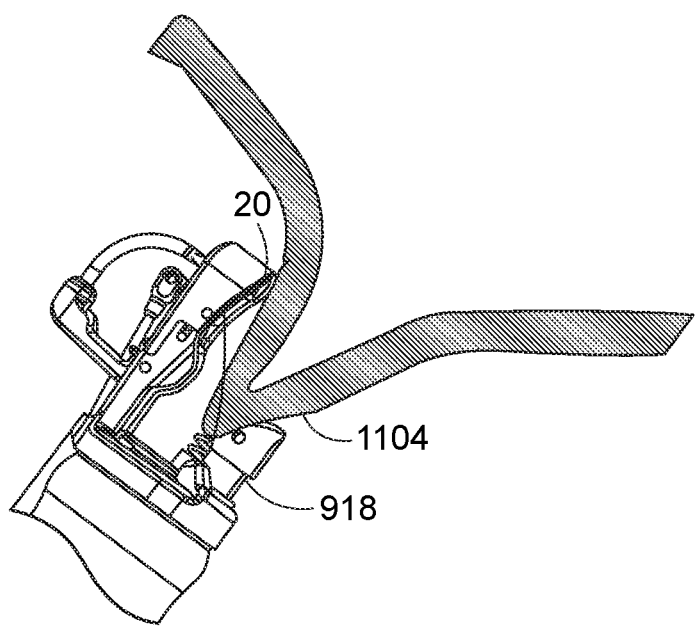

A tissue-grasping instrument 900, as previously briefly described and described in detail in previously incorporated U.S. Pat. No. 8,679,136 to Mitelberg, is advanced through a second instrument channel (not shown) of the endoscope 712 and beyond the distal end of the endoscope and the cap assembly 733. The tissue-grasping instrument 918 is operated to engage the stomach lining 794 at the lateral portion of the stomach at a first location 1104, preferably relative to one of the guidelines $G_A$, $G_P$, or along another lateral guideline (FIGS. 28A and 28B), and draw the first location 1104 into the path of the first needle 20 (FIGS. 33 and 34).

Figure 35:
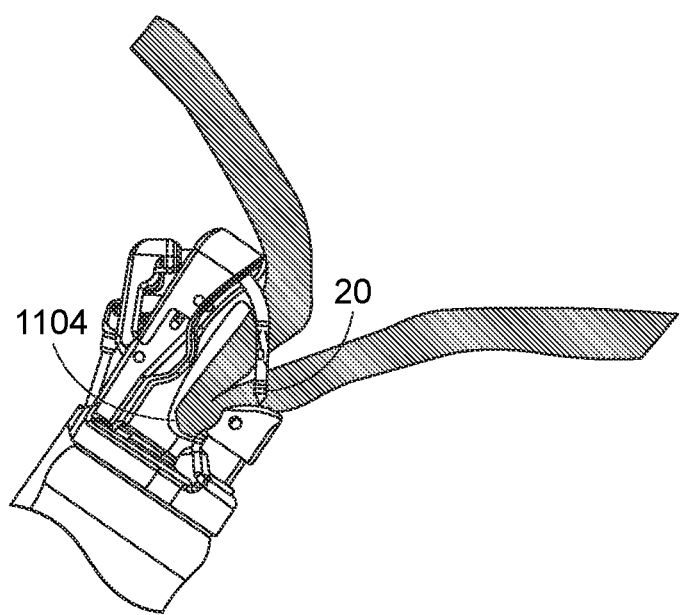
Figure 36:
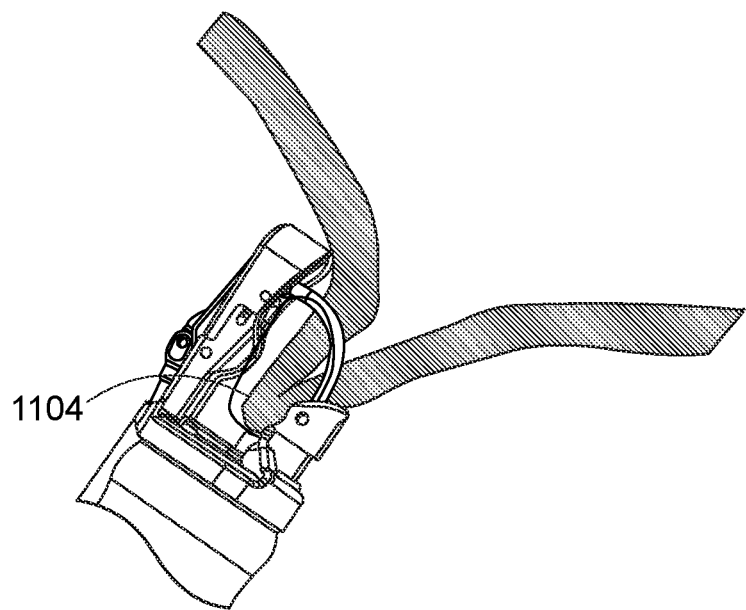
Figure 37:
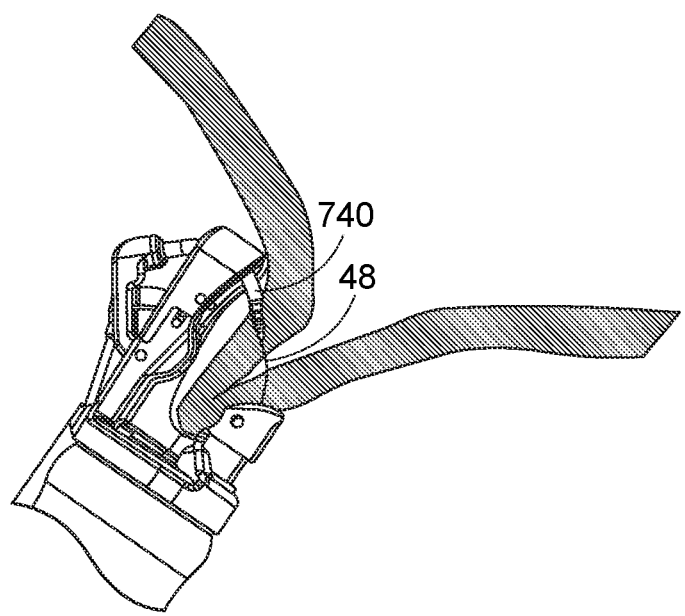
Figure 38:
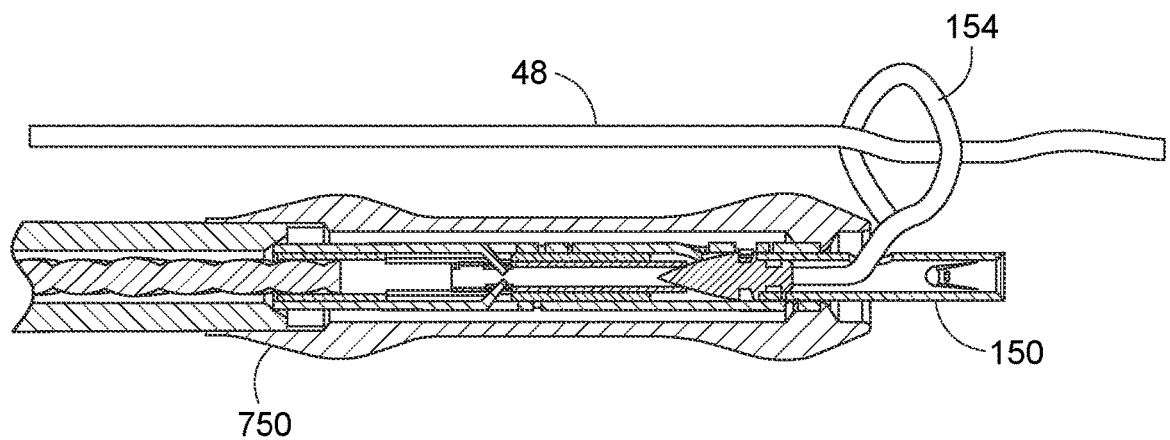

Referring to FIGS. 35 and 36, the cap assembly 733 is then operated from outside the body to move the first needle 20 along its needle path toward and into a closed position, thereby piercing the first needle 20 and elongate suture 48 through the engaged first tissue location 1104 and passing the first needle back into the distal end of the needle exchange device 750 (not shown) in the first instrument channel. The needle exchange device 750 is then re-engaged with the piercing end 20b of the first needle, and the first needle is retained relative to the needle exchange device while the needle holder arm 740 is retracted out of engagement with the first needle (FIG. 37). The tissue-grasping instrument is then released from the tissue. In addition, the needle exchange device is opened to release its engagement from the first needle, and the needle exchange device is withdrawn from the first instrument channel. The first needle 20 is consequently in a position where it has been advanced through the first tissue location 1104 at a distal location of the stomach, and its elongate suture 48 extends through the first tissue location and back down through the first instrument channel (FIG. 38).

Figure 39:
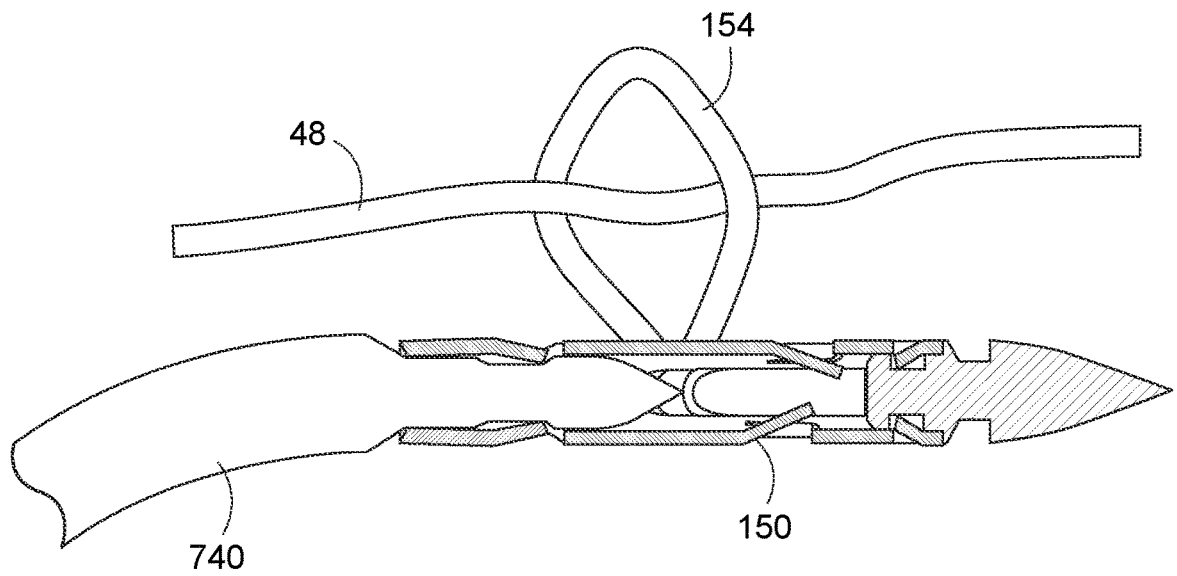
Figure 40:
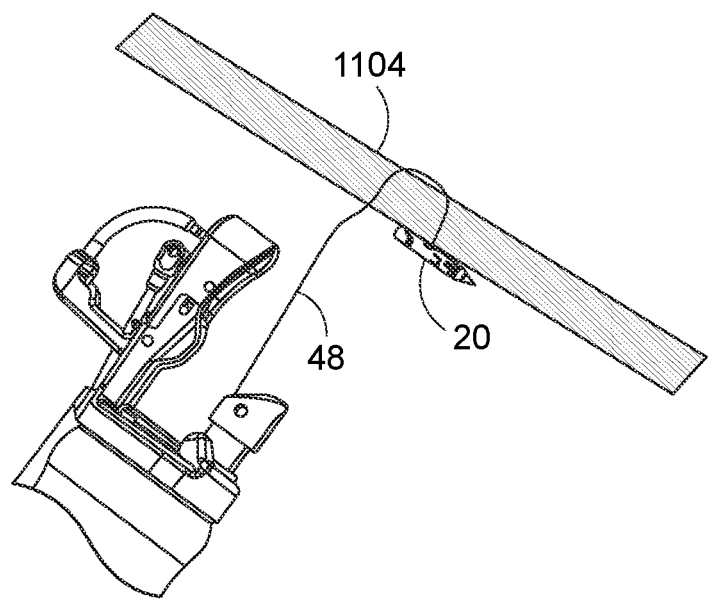

Referring to FIG. 39, a second needle 150 is then engaged relative to the needle exchange device 750 from outside the patient's body. The proximal end of the elongate suture 48 is inserted through the opening of the second needle; i.e., the loop 154. The second needle 150 is then advanced through the first instrument channel over the elongate suture 48 with the suture loop 154 extending over the elongate suture. Then, as shown in FIG. 40, the second needle is transferred to the needle holder arm 740, in the same process described with respect to the first needle 20, all while the elongate suture 48 continues to extend through the loop 154.

Figure 41:
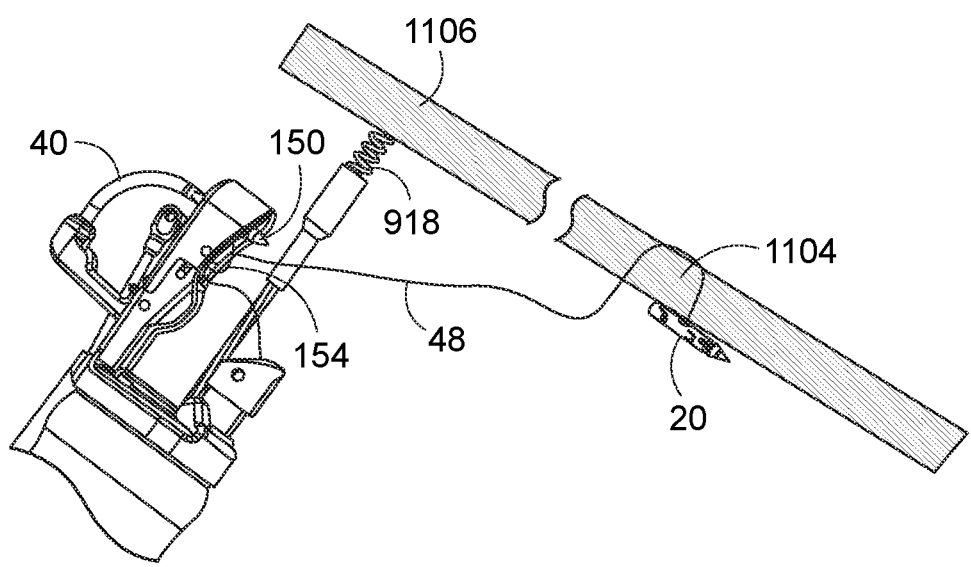
Figure 42:
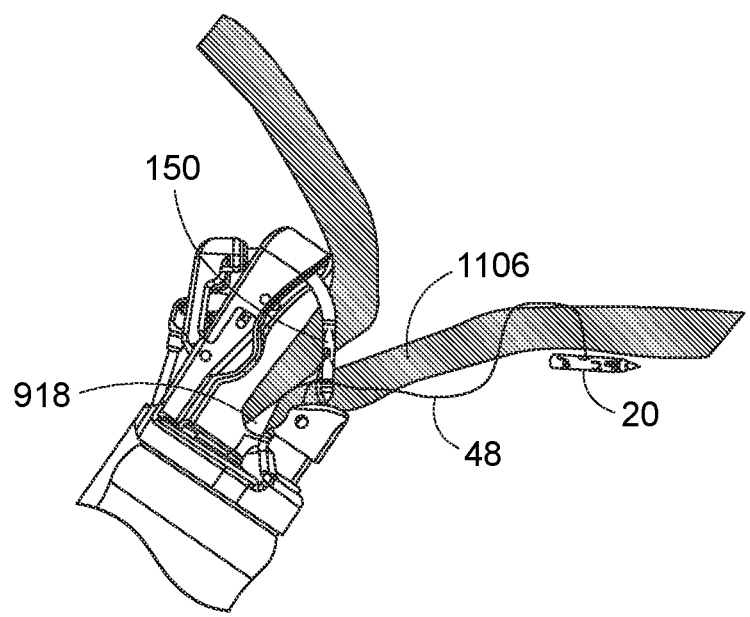
Figure 43:
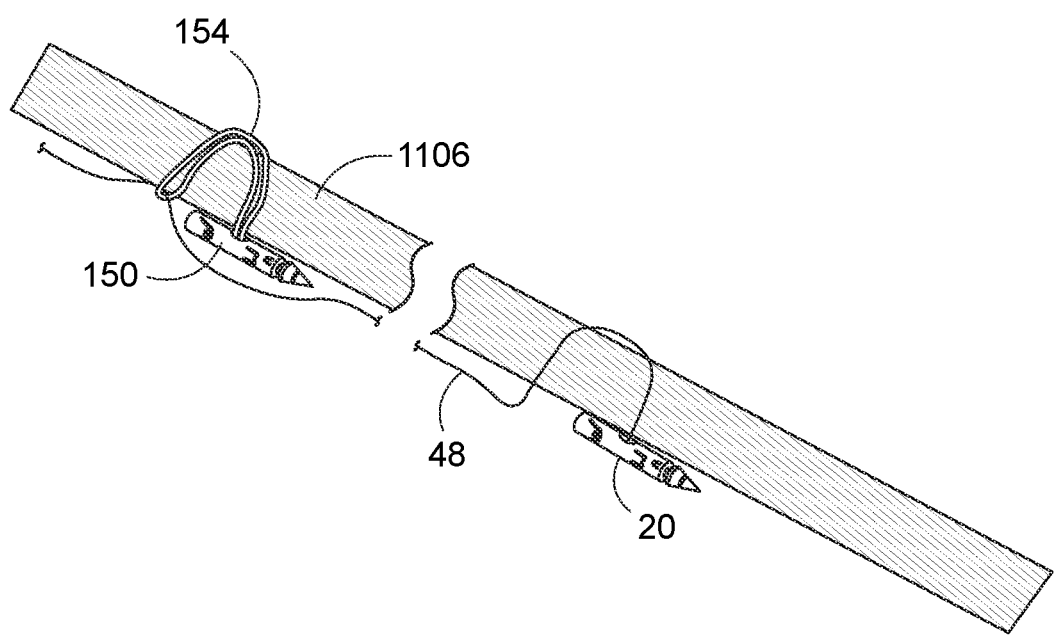

Turning now to FIG. 41, the distal end of the endoscope is then maneuvered toward a second tissue location. In accord with one preferred gastric reduction procedure, such second tissue location is preferably proximally-displaced and radially-displaced relative to the first tissue location. As shown in FIG. 42, a similar process as with the first needle 20 is then effected to engage the second tissue location 1106 with the tissue grasper 918, draw the second tissue location 1106 into the path of the second needle 150, and cause the second needle to pierce the second tissue location. The second needle 150 is then released at the second tissue location 1106 (FIG. 43), at a location displaced from the first needle 20. The elongate suture 48 of the first needle remains extending through the suture loop 154 or other opening of the second needle.

The same process for second-type needle advanced and tissue insertion is repeated for one or more other needles of the same type as the second needle; i.e., a needle that can be advanced or having a suture loop that can be advanced over the elongate suture of the first needle, at additional third, fourth, etc. tissue locations. Preferably, the third tissue location is proximally-displaced and radially displaced relative to the second tissue location.

Figure 44A:
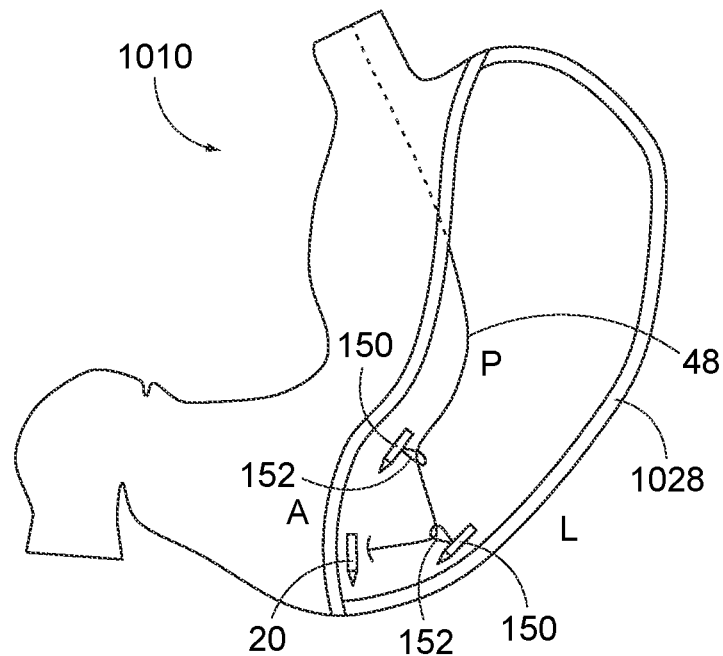
Figure 44B:
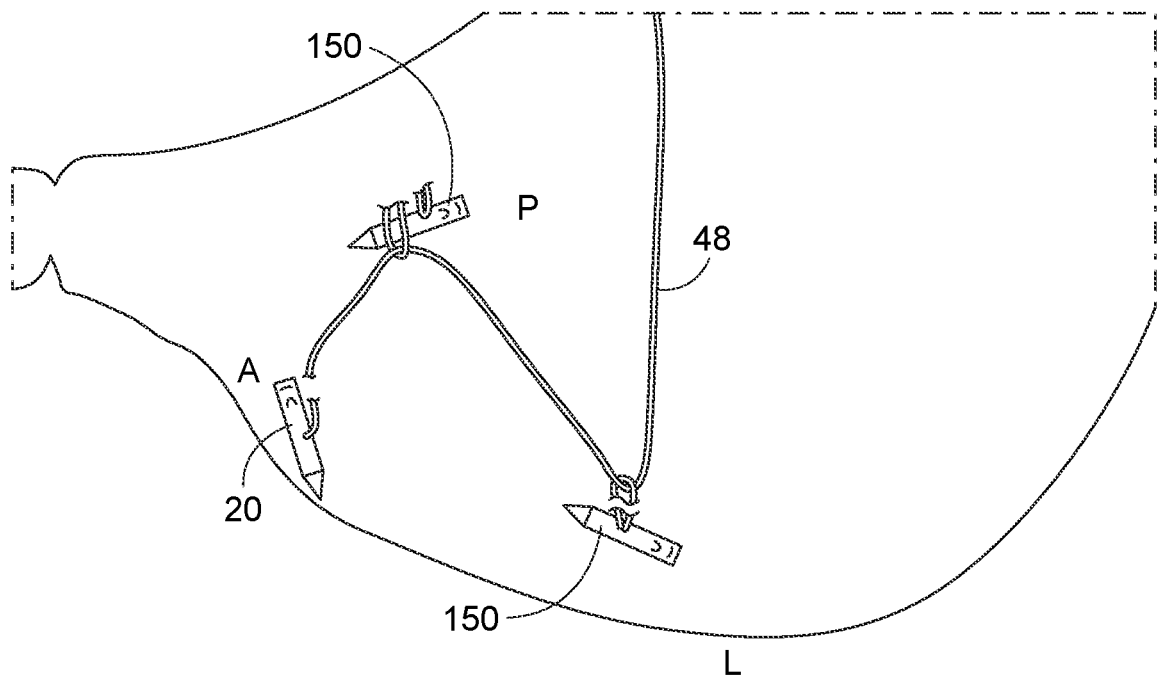
Figure 45A:
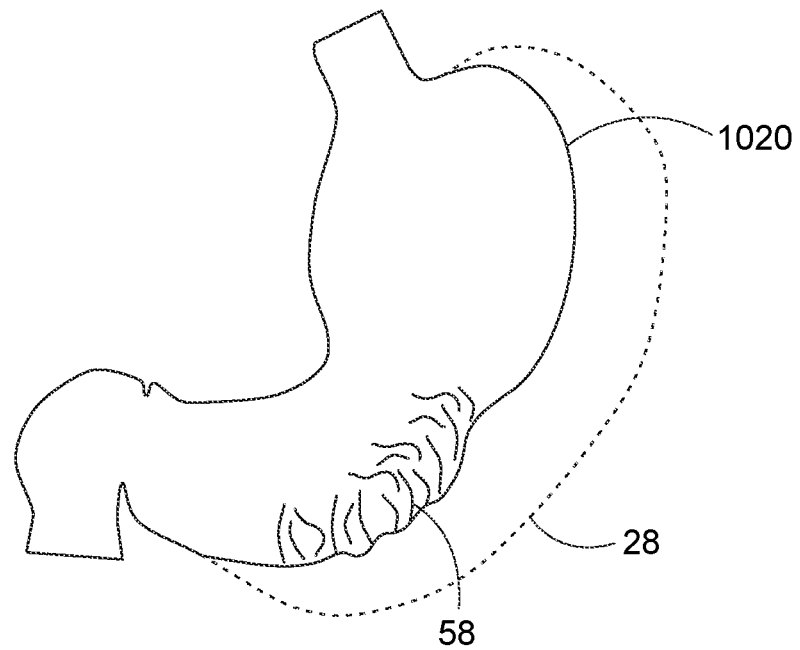
Figure 45B:
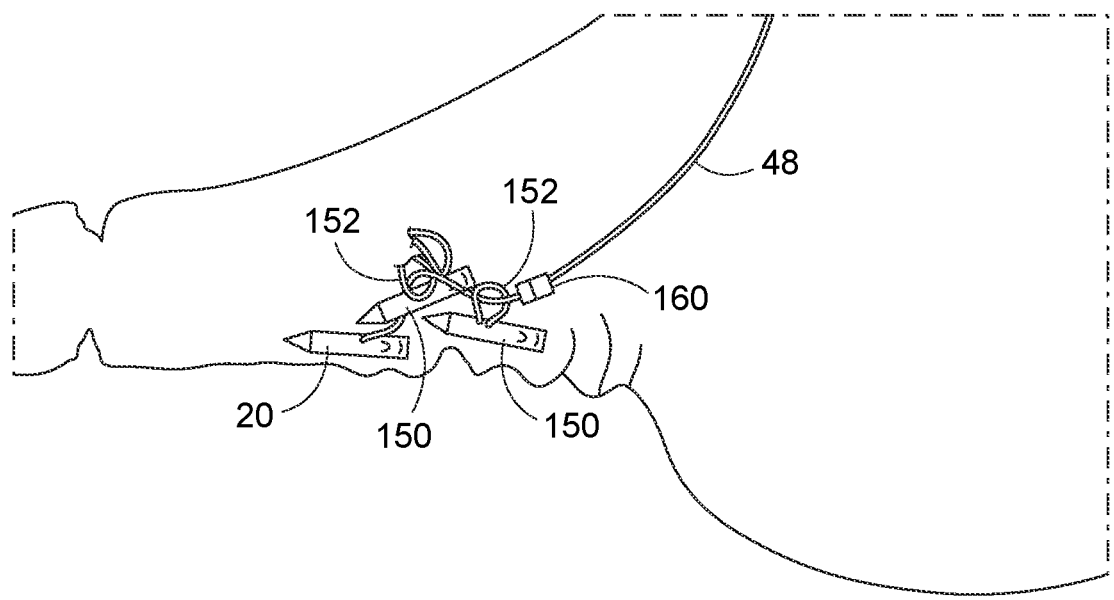

Turning now to FIGS. 44A and 44B, with the insertion of a first needle with elongate suture, and at least two second-type needles 150, the anterior (A), lateral (L), and posterior (P) sides of the greater curve 1028 of the stomach 1010 are engaged. The common elongate suture 48 running from the first needle running 20 to the additional second-type needles 150 at their respective tissue engagement locations is then pulled taut through the openings 152 of the second-type needles to cause the second type needles to collapse inward toward the first needle, like a purse string (FIGS. 45A and 45B). The elongate suture 48 is then secured, e.g., cinched with cinch 160, clipped, tied off, or otherwise, to retain this tissue-collapsed configuration. By way of example only, a suitable cinch 160 that can be secured onto suture 48, that can maintain the tensioned configuration of the elongate suture 48 relative to the second-type needles 150, and which can be inserted through an endoscope working channel is disclosed in co-owned U.S. Pat. No. 8,540,735.

The method is then repeated at a proximal location to the cinched location; i.e., to gather and retain additional tissue to reduce the effective size of the stomach. As the anterior, lateral and posterior portions of the stomach are cinched together with the elongate suture pulling against the second-type suture needles, such cinching causes the fundus 1020 to be automatically drawn downward to effectively shorten the length of the fundus. As the shape of the fundus 1020 is altered, the fundus can be subsequently approached for suturing by pulling back the endoscope to an ever proximal location and without retroflexing the endoscope. Further, other instruments are not required for the suturing process. In this manner, the method facilitates access to the anatomy, and particularly the fundus, relative to prior art incisionless stomach reduction procedures. In addition, the devices and methods described herein facilitate engaging the stomach tissue are desirable locations, and reducing the capacity of the stomach tissue utilizing capture of such engaged locations.

That is, if necessary or desirable, additional second-type needles then can be advanced over the same secured elongate suture of the first needle to engage additional tissue locations. The elongate suture can then be pulled taught again relative to the previously tied off or clipped location of the elongate suture to secure such second-type needles and their engaged tissue locations together. Once all needles that are desired to be advanced over the elongate suture of the first needle have been so located at their respective tissue locations, and such tissue locations have been secured together, the remaining elongate suture can be cut free from the suture site with a knife, scissors, or cinching instrument and withdrawn from the first instrument channel. Additionally or alternatively, another first-type needle can be advanced through the first instrument channel and additional second-type needles can be advanced thereover, in the same manner as previously described. In addition, rather than pull taut and securing the elongate suture of the first applied first needle, and then insert a second first-type needle, all needles—first and second types—can be first inserted into the stomach tissue, and thereafter the elongate sutures of the first type needles can be pulled taut to cinch together the second type needles. In this manner, all of the needles are inserted with the stomach in its full size with greatest visibility to the surgeon; once the needles are secured, the stomach is collapsed by pulling the elongate sutures in turn, preferably from the most distally-placed suture to the most proximally-placed suture.

Furthermore, while the first needle with a standard suture structure can be utilized in the procedure, it is recognized that any of the other elongate suture structures described herein can be used. That is, the method can include the use of an elongate suture having retention structure, for example, barbs or beads or teeth extending along at least a portion of its length. When the elongate suture is pulled taut and through the openings of the second-type needles, the barbs, beads or teeth engage relative to the second needle opening structure to prevent the elongate suture from backing off. Moreover, where the second needles include suture loops that are cinchable or reducible in size, each can be cinched against the retention structure to form a loose or secure hold. Also, where the second needle is provided with a latch at the suture opening, such latch structure can be employed to securely engage the retention structure of the elongate suture. In view of the above, various options are provided for retaining the stomach wall tissue in a collapsed configuration to effect a gastric reduction.

It is anticipated that three to seven helical windings of suture are required to fully draw in and collapse the greater curve of the stomach. Given the use of the potentially multiple second needles in association with the single elongate suture of a first needle, (i) a greater number of needles than windings may be used, (ii) a greater number of second needles than windings may be, and (iii) potentially (given that a first needle with elongate suture can be used to generate a plurality of windings) fewer first needles than windings may be used.

Figure 46:
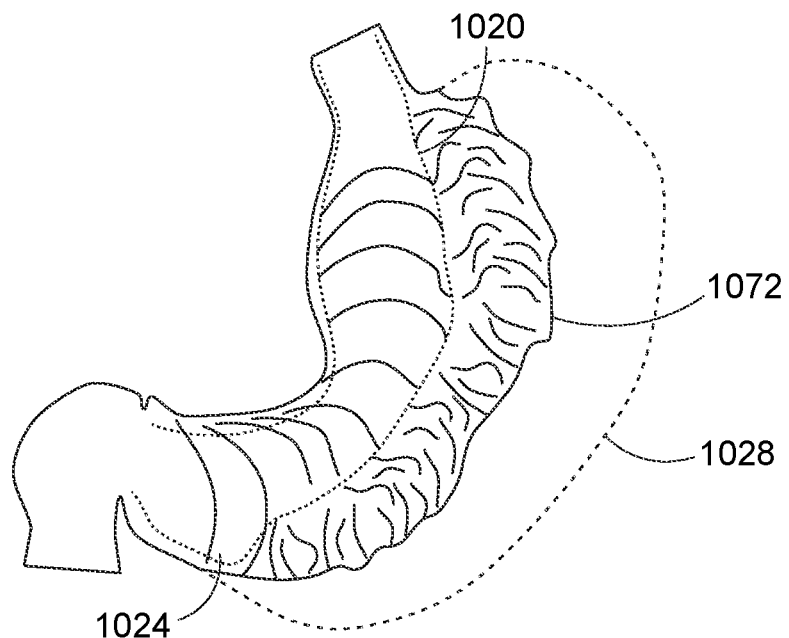
Figure 47:
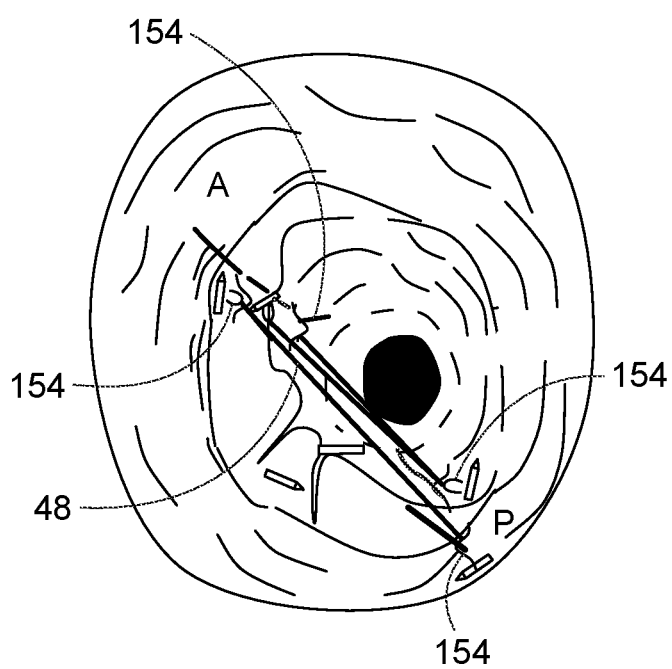
Figure 48:
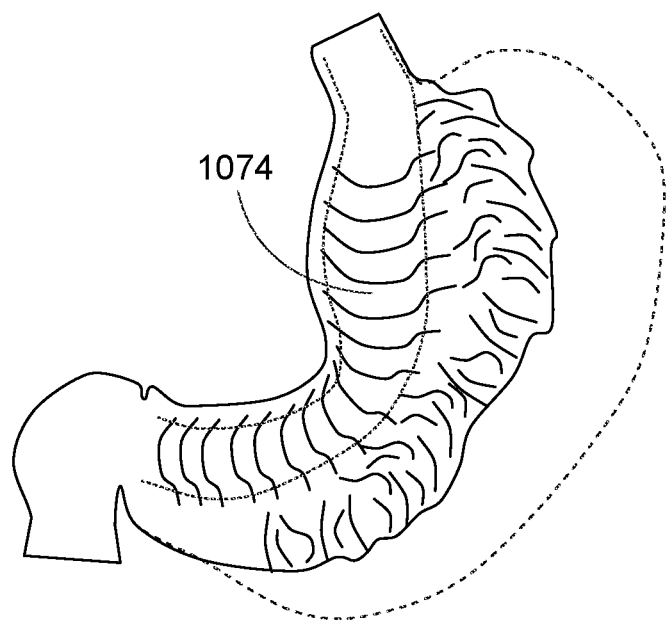

Turning now to FIG. 46, after the greater curvature 1028 is collapsed, a running row of a suture stitches is advanced from the antrum 1024 to the fundus 1020 along the collapsed portion 1072 of the stomach. It is preferred that a continuous vertical row of stiches be provided through the stomach alternating in the anterior-posterior direction; e.g., by engaging the anterior side of the stomach wall with a suture, then passing the suture through the posterior side at a vertically higher location, then passing the suture back through the anterior side at a vertically higher location than engaged at the posterior, and so on. The suture in this step may be one or more elongate sutures 48 from respective first-type needles. Alternately, referring to FIG. 47, the row of stitches may be formed much in the manner the helically displaced stitches were presented; i.e., with a first type needle inserted at a distal location, and two opposing rows of second-type needles advanced over the elongate suture of the first type needle. After the suture 48 is threaded through several locations in the alternating anterior-posterior arrangement of the suture loops 154, the suture is cinched to draw the anterior and posterior sides of the stomach wall together to define a relatively smooth passage 1074 between the lesser curvature and the now stitched tissue, as shown in FIG. 48. The passage 1074 preferably excludes the approximation of the previously stitched anterior, posterior, and lateral sides. Once the row is complete, several advantages are provided. The row of stitches secures the prior reshaping of the stomach. The row of stiches further reduces the size of the stomach. The row of stitches provides a smoother and more well-defined passage 1074 from the upper to the lower ends of the stomach.

Figure 49:
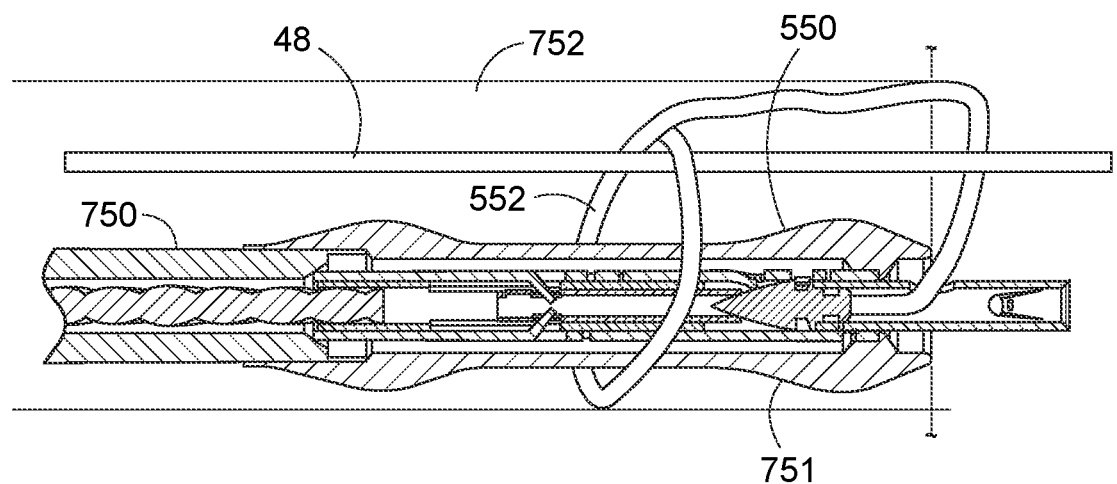
FIG. 49 illustrates the needle exchange device within a working channel of an endoscope and loaded with a second-type needle having a suture loop extending about an elongate suture of a first-type needle.
Figure 50:
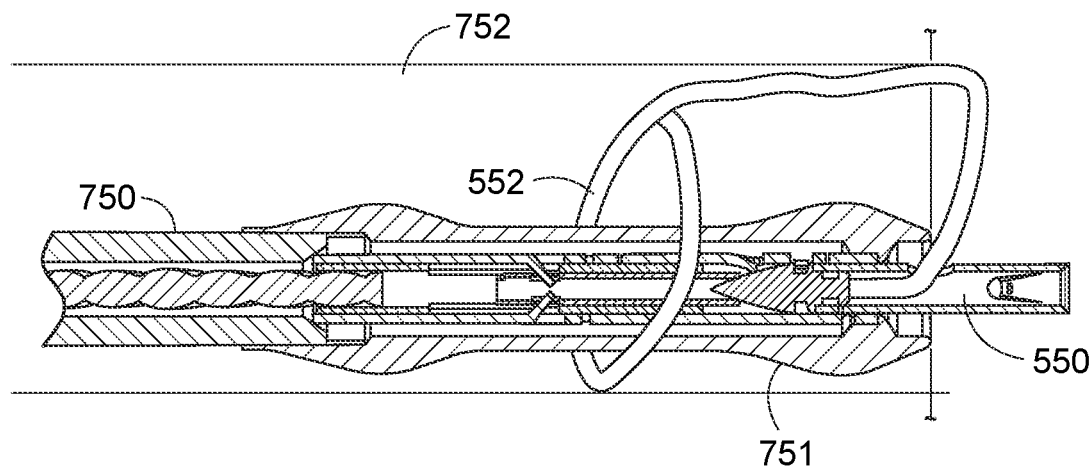
FIGS. 50 and 51 illustrates the needle exchange device within a working channel of an endoscope and loaded with embodiments of second-type needles having suture loops.
Figure 51:
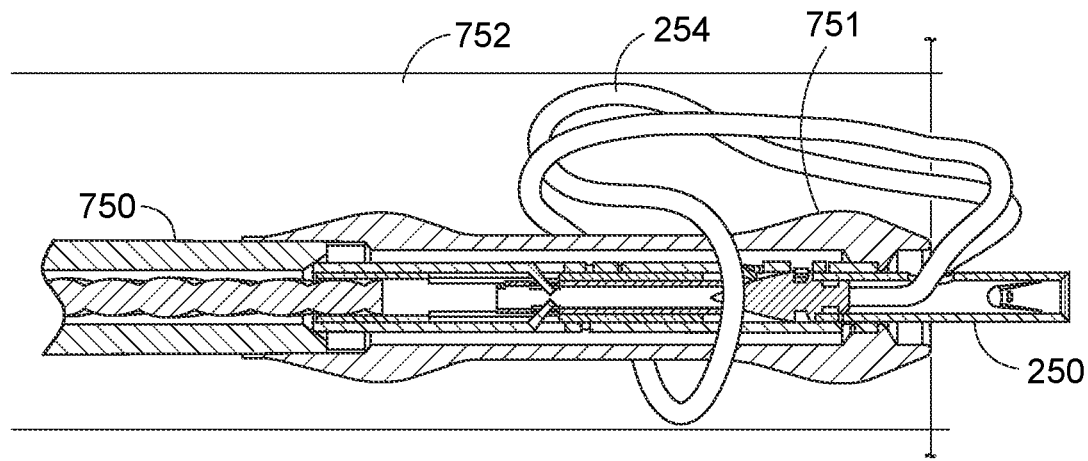

Turning to FIGS. 49-51, in accord with another aspect of using the second-type needle, the second-type needle can also be advanced within the working channel 752, with its suture loop provided about a portion of the needle exchange device 750, e.g., a distal needle housing 751 (i.e., the portion of the needle exchange device in which a needle is captured and carried). Referring to FIG. 49, a suture loop 552 of a second-type needle 550, when positioned over the distal needle housing 751, can also be provided over the elongate suture 48 of a first-type needle (not shown). Alternatively, with reference to FIG. 50, the second-type needle can be delivered within the needle housing 751 of the needle exchange device, with the suture loop 552 positioned about the needle housing, and without advancement over the elongate suture of a first-type needle. FIG. 50 illustrates such configuration using the exemplar second-type needle of FIG. 23. Similarly, FIG. 51 illustrates a second-type needle 250 having a loop 254 of suture extending from the needle body, with a portion of the loop 254 positioned over the needle housing 751, all within the working channel 752.

Figure 52:
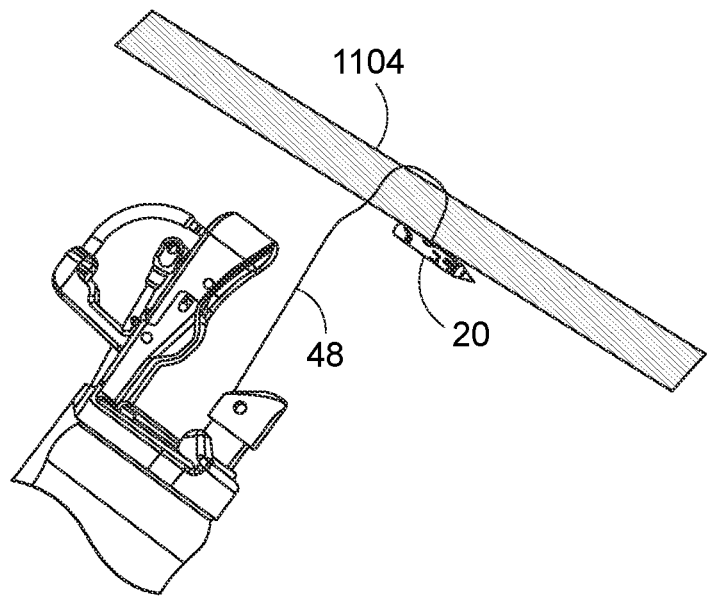
FIGS. 52 through 57 illustrate another method of applying suture needles and suture into tissue.
Figure 53:
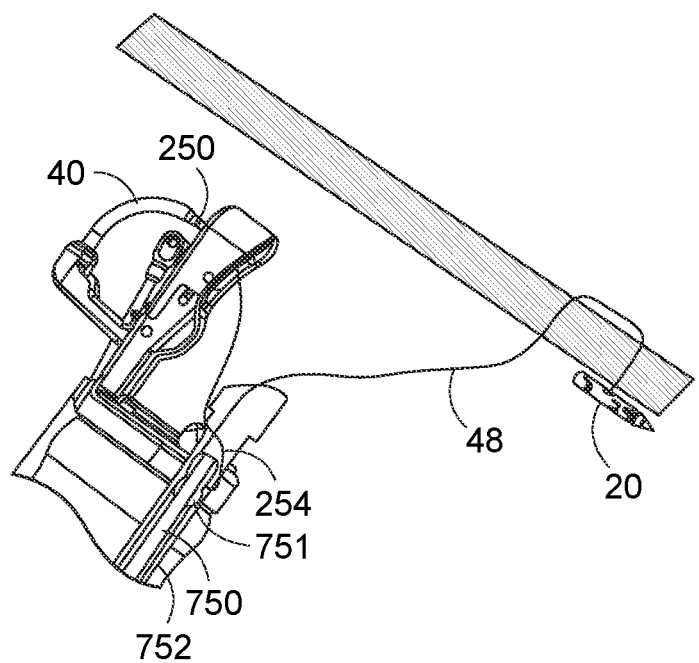
Figure 54:
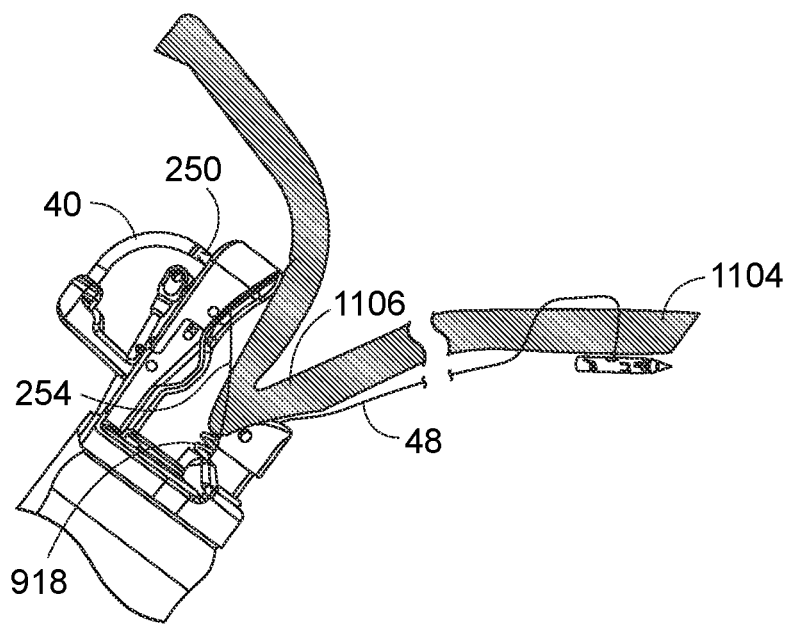
Figure 55:
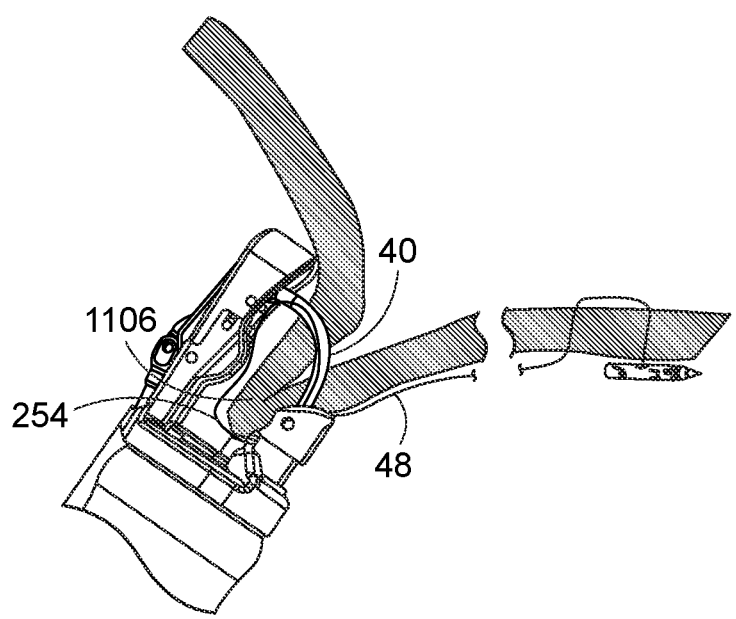
Figure 56:
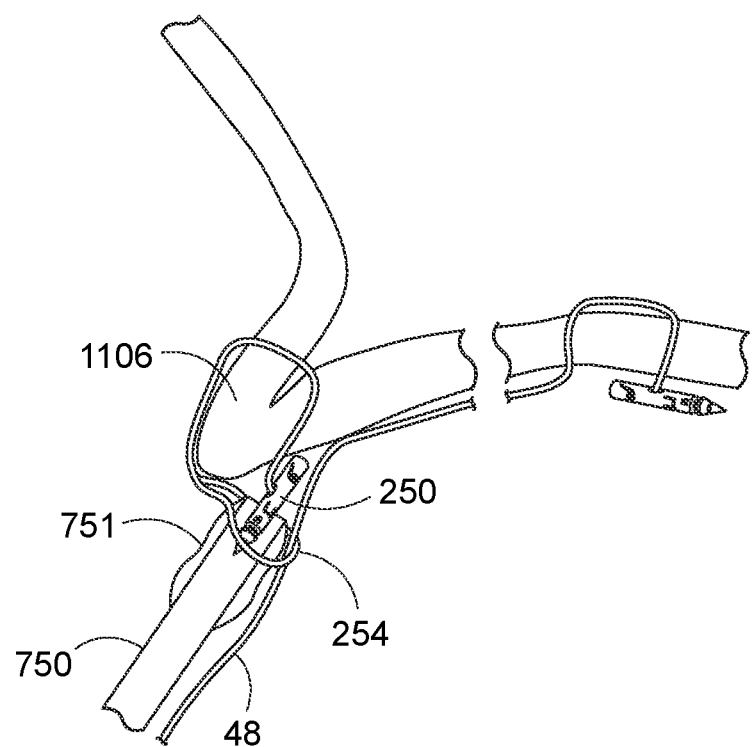
Figure 57:
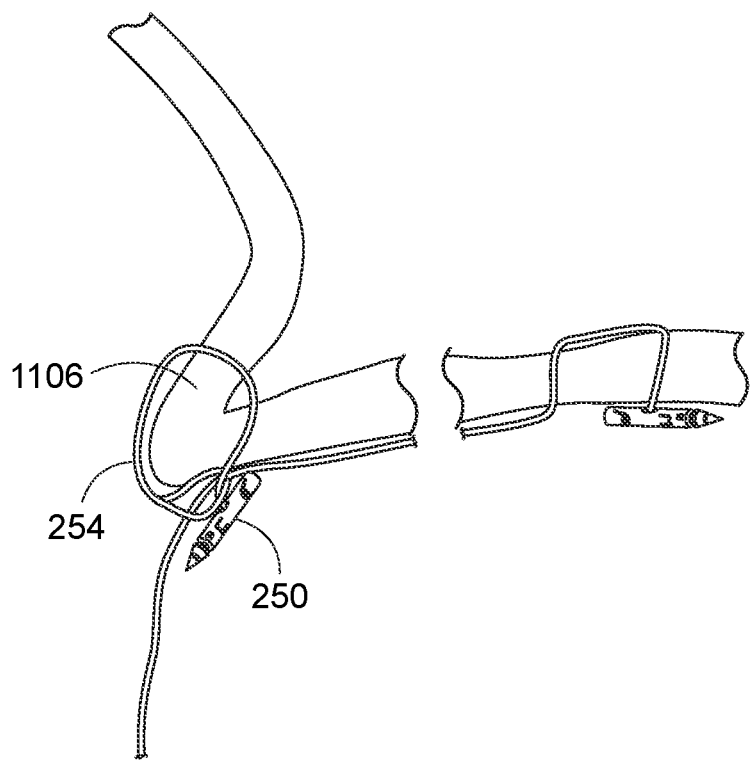

Configuring the loop of the second-type needle about the needle housing 751 housing of the needle exchange device 750 permits securing the second fastening in a different manner relative to that described above. Specifically, the loop of the second-type needle can be looped over the body of the second-type needle to provide a secure retention. By way of one example in which the second-type needle is used in conjunction with a first-type needle, reference is now made to FIGS. 52-57. In FIG. 52, a first-type needle 20 is shown coupled to tissue 1104, such as taught with respect to FIG. 40, above. Then, the needle exchange device 750 is loaded with a second-type needle 250, in which the loop 254 of the second type needle is positioned over the elongate suture 48 and the needle housing 751, and the needle exchange device with second-type needle are then advanced back down the working channel. The needle holder arm 40 is then closed relative to the needle exchange device 750 and the second type needle 250 is transferred to the needle holder arm. The needle holder arm 40 is then opened, while the suture loop 254 of the second-type needle is retained about the needle housing 751 in the working channel 752 of the endoscope (FIG. 53). A tissue grasper 918 is then used to pull tissue 1106 into the path of the needle 250 in the needle holder arm 40 (FIG. 54). The needle holder arm 40 is then operated from the proximal end of the instrument to advance the second-type needle 250 through the grasped tissue 1106. The passed second-type needle 250 is captured in the needle capture device. (FIG. 55) The needle holder arm 40 is then re-opened to release its engagement relative to the passed needle 250. (FIG. 56, which illustrates the described state with endoscope and end cap assembly removed from the illustration for clarity.) The needle exchange device 750 is then retracted or maneuvered from its proximal end, to any extent necessary, to pull the second-type needle 250 completely through the loop 254 coupled thereto. The second-type needle 250 is then released from the needle exchange device and retained at the tissue 1106.

While the first and second needles, with their respective sutures, thus far have been described particularly with respect to gastric reduction, it will be appreciated that such systems can be used to perform other procedures within the mammalian body.

By way of example, other natural tissue or an implanted device can be secured. Such an implanted device can include, by way of example, a stent or pledget.

Figure 58:
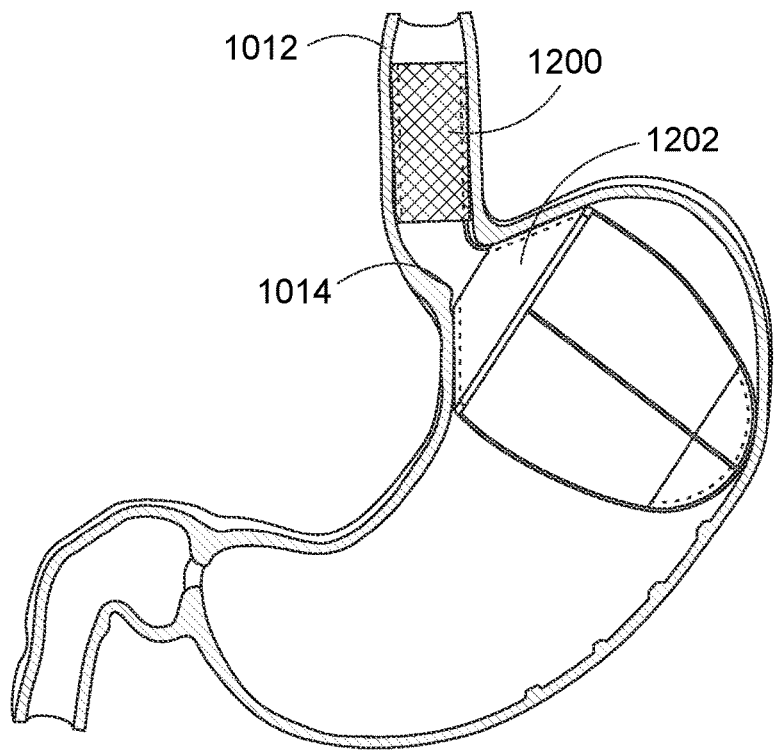
FIG. 58 illustrates a partial broken view of an implant located within the esophagus and stomach.

In one example, the suture needle system described herein can be used to secure a stent in the gastrointestinal tract. More particularly, referring to FIG. 58, a gastroesophagheal stent 1200 is shown positioned in the esophagus 1012 adjacent the gastroesophageal junction (GEJ) 1014. The stent 1200 may optionally be coupled to a gastric implant 1202 that increases pressure against the cardia and/or which is adapted to partially fill the stomach, to thereby reduce the available space within the stomach, each of which is adapted to cause an increased sense of satiety to a patient. Alternatively, the gastric implant can be a duct extending from the gastroesophageal junction 1014 to the pylorus to completely bypass the stomach. Regardless, it may be advantageous to secure the implant to the esophageal, stomach, or GEJ wall with a fastener such as a needle.

Figure 59:
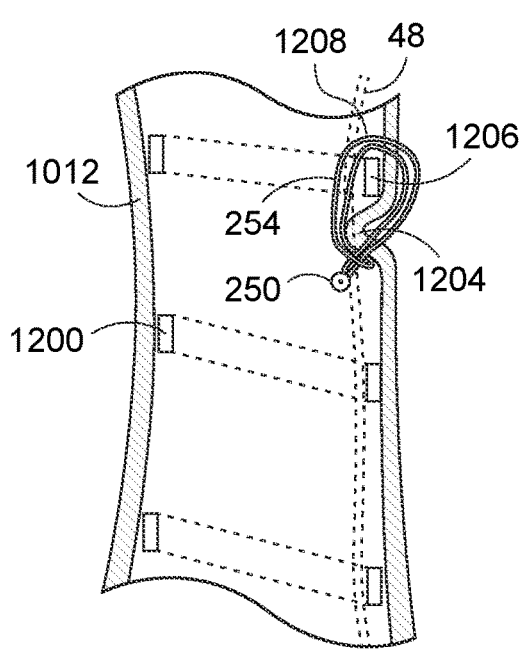
FIG. 59 is a longitudinal broken section view of a stent implanted in the esophagus and secured by a second-type needle.
Figure 60:
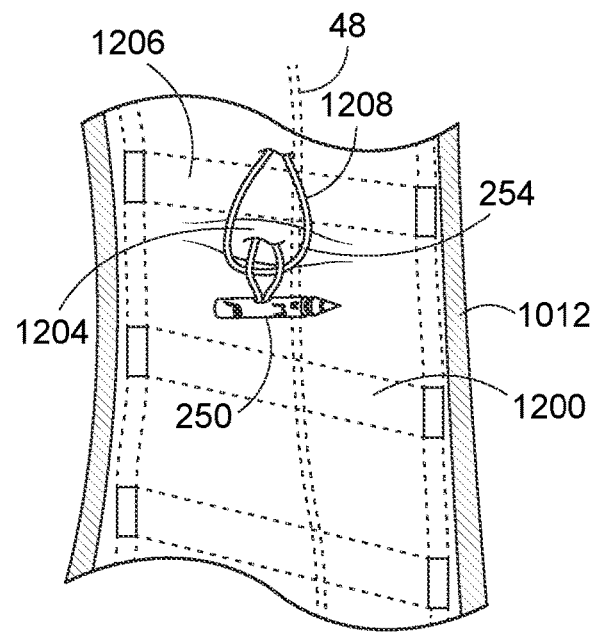
FIG. 60 is a longitudinal broken section view, rotated 90° relative to FIG. 59 of the stent implanted in the esophagus and secured by the second-type needle.

Procedures described above for securing tissue can similarly be used to secure an implant, such as a stent, to tissue. That is, tissue can be engaged relative to a portion of the stent 1200, and a needle with suture is used to secure of portion of the stent relative to the tissue. In one method, only second-type needles are used. The tissue is engaged near a structural element of the stent. The needle 250 is advanced through the tissue 1204 and around the structural element 1206 of the stent, and the loop 254 of suture is positioned over the needle and the needle is pulled through the loop to secure the needle relative to the tissue. (FIGS. 59-60) This procedure forms a loop 1208 around the structural element 1206 of the stent to retain the stent in position relative to the tissue 1204. Additional second-type needles can be applied, as necessary, to further secure the stent to the anatomy. In addition, the second-type needles can be advanced over earlier secured elongate suture of a first-type needle 48; however, such is not necessary.

Figure 61:
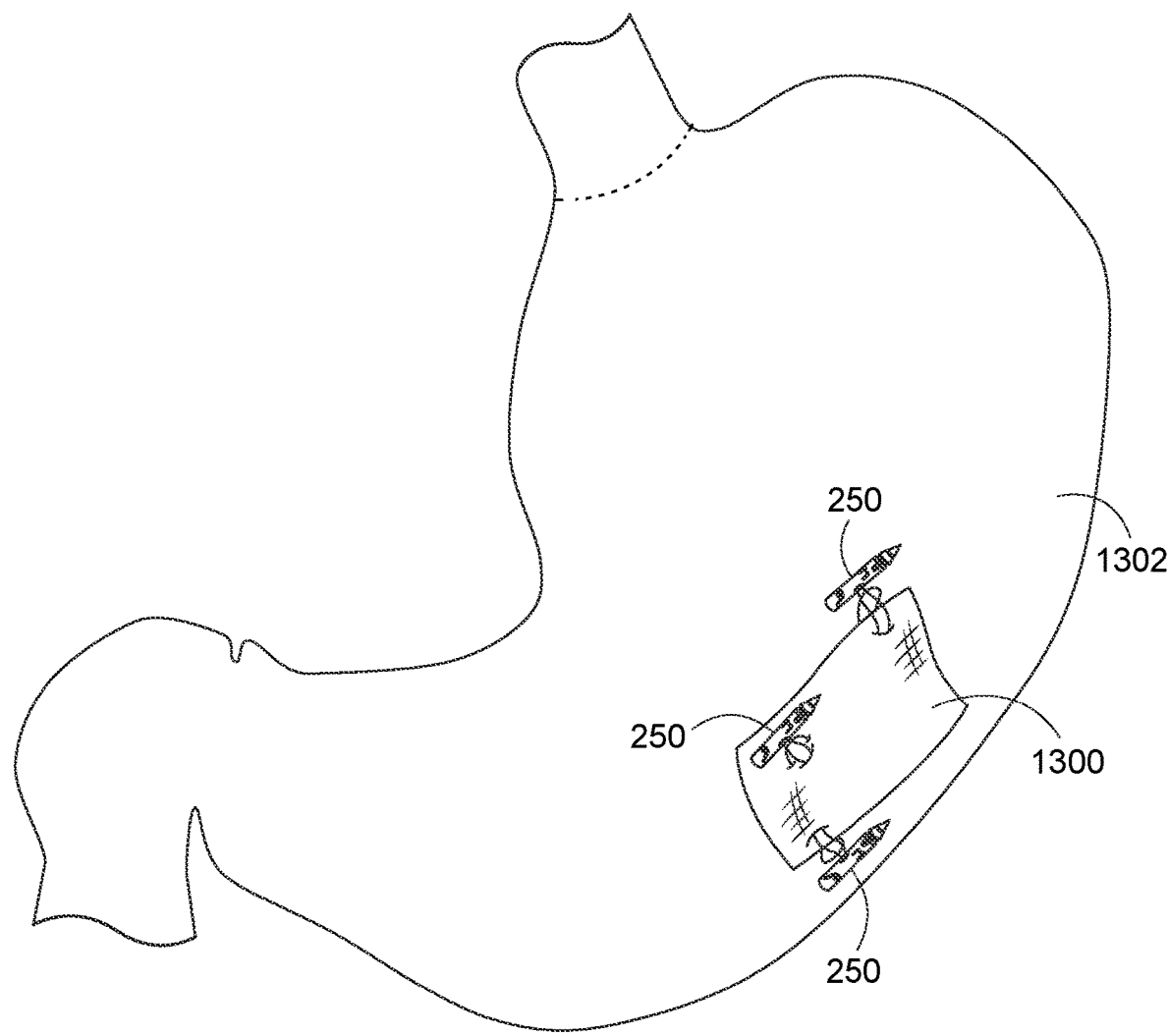
FIG. 61 is a schematic view of the stomach with a pledget implanted within the stomach tissue with second-type needles.

Turning to FIG. 61, in another example, the suture needle system can be used to secure a pledget 1300 to tissue. Pledget 1300 is shown secured to stomach tissue 1302 in a manner similar to that in which a stent 1200 (FIGS. 59 and 60) is secured to tissue. One or more suture needles can be used to secure a pledget.

Implants can be secured to tissue with (i) one or more first-type needles and elongate suture only, (ii) one or more second-type needles and suture loops only, or (iii) a combination of first- and second-type needles with their respective suture constructs.

As another example, the second needles can be permanently or temporarily implanted in tissue for at least the purposes of (i) to provide visualization of tissue locations to the surgeon and/or (ii) to position tissue at desired locations.

The procedures described herein provide better durability and enables new stitching patterns. In addition, because the stitch guidelines can remain visible during the procedure, the surgeon can better orient the tools to the target tissue, thereby facilitating completion of the procedure.

The present invention has been described in conjunction with the exemplar embodiments shown in various drawings. However, the invention should not be limited to the selected embodiments shown and described. By way of example, other retaining structure to prevent or inhibit the second needle from displacing along the elongate suture can also be used. Also, additional or alternative structure to allow the second needle to be received over and/or relative to the first needle can be employed, including alternative structure to a cinch or a latch that can be bear down on or engage the elongate suture. Moreover, while the structural embodiments have been described with respect to a gastric reduction procedure, it is appreciated and within the scope hereof that such structure may be used for different procedures as well as at other locations within the mammalian body. It will therefore be appreciated by those skilled in the art that yet other modifications could be made to the provided invention without deviating from its scope as claimed.

What is claimed is:

1. A method for suturing tissue, said method comprising:
providing a first needle having an elongate first suture with a free proximal end and a distal end attached to the first needle;
inserting the first needle into tissue at a first location;
providing a second needle defining a suture passage opening;
positioning the suture passage opening over the proximal end of the elongate first suture;
advancing the second needle over the elongate first suture;
inserting the second needle into tissue at a second location displaced from the first location; and
pulling the elongate first suture of the first needle taut through the suture passage opening of the second needle to cause the first and second needles to be brought into closer proximity.

2. The method of claim 1, further comprising:
providing a second suture having a first end and a second end that are fixed with respect to the second needle, and a loop formed between the first end and the second end of the second suture; and
allowing the loop to be advanced over the elongate first suture when the second needle is advanced over the elongate first suture.

3. The method of claim 1, further comprising:
providing a second suture with a looped portion; and
allowing the looped portion to be advanced over the elongate first suture when the second needle is advanced over the elongate first suture.

4. The method of claim 1, further comprising:
providing a second suture having a first end fixed relative to the second needle, and an opposite second end, and a loop portion at the second end of the second suture; and
allowing the loop portion to be advanced over the elongate first suture when the second needle is advanced over the elongate first suture.

5. The method of claim 4, further comprising adjusting a dimension of the loop portion after the loop portion is advanced over the elongate first suture.

6. The method of claim 4, further comprising cinching the loop portion after the loop portion is advanced over the elongate first suture.

7. The method of claim 1, further comprising:
providing a second suture with an opening defined within a latch mechanism fixed at a second end of the second suture;
wherein:
the elongate first suture includes a plurality of longitudinally displaced catches for the latch mechanism; and
the latch mechanism engages the catches when the second needle is advanced over the elongate first suture in a proximal to distal direction to inhibit retraction of the second needle relative to the first needle.

8. The method of claim 1, further comprising reducing a diameter of a retaining structure to engage the elongate first suture between two longitudinally displaced retaining structures.

9. The method of claim 1, further comprising inserting the first needle endoluminally through an esophagus and into a stomach, wherein:
the first and second locations of tissue are locations within the stomach, and
when the first and second needles are brought into closer proximity, the volume of the stomach is reduced.

10. The method of claim 1, wherein the method is incisionless.

11. The method of claim 1, further comprising:
advancing a suture cinch over the elongate first suture; and securing the suture cinch on the elongate first suture to prevent the second needle from retracting along on the elongate first suture.

12. The method of claim 1, further comprising:
providing a third needle defining a suture passage opening;
positioning the suture passage opening of the third needle over the proximal end of the elongate first suture;
advancing the third needle over the elongate first suture;
inserting the third needle into tissue at a third location displaced from the first and second locations; and
pulling the elongate first suture of the first needle taut through the suture passage opening of the third needle to cause the third needle to be brought into closer proximity with at least one of the first or second needle.

13. The method of claim 12, further comprising inserting the third needle into tissue prior to pulling the elongate first suture of the first needle taut, such that when the first suture is pulled taut, the first, second, and third needles are brought into closer proximity.

14. The method of claim 12, further comprising inserting the first, second, and third needles into tissue at helically displaced locations.

15. A method of implanting an implant in tissue endoscopically, said method comprising:
advancing an implant through an endoscope to be adjacent a tissue wall;
advancing, through the endoscope, a first needle having a first suture loop coupled thereto;
advancing the first needle with the first suture loop through the endoscope to adjacent the implant; and
inserting the first needle into the tissue wall, and extending the first suture loop about a portion of the implant to retain the implant relative to the tissue wall.

16. The method of claim 15, further comprising positioning a second needle through the first suture loop.

17. The method of claim 15, further comprising:
before providing a first needle having a first suture loop, providing a needle having an elongate suture with a free proximal end and a distal end attached to the needle having the elongate suture;
inserting the needle having the elongate suture into the tissue wall; and
allowing the first needle having a first suture loop to be advanced over the elongate suture when the first needle having a first suture loop is advanced to adjacent the implant.

18. The method of claim 15, wherein said method is performed fully endoscopically.

19. A method of suturing tissue with a system including an endoscope having a working channel with proximal and distal ends for passage of an instrument, and a suturing assembly mounted at the distal end of the endoscope, the suturing assembly having a needle holder arm that is rotatable from the proximal end of the endoscope into coaxial arrangement with the working channel, said method comprising:
providing a needle exchange device insertable within the working channel, the needle exchange device having a distal housing for receiving a suture needle, a needle received in the distal housing, the needle having a suture loop permanently coupled thereto, wherein the suture loop is positioned around the outside of the distal housing;
advancing the needle exchange device into the working channel until the needle reaches the distal end of the working channel;
rotating the needle holder arm in a first direction toward the working channel and into engagement with the needle, and releasing the needle from the needle exchange device;
rotating the needle holder arm in an opposite second direction away from the working channel to move the needle away from the working channel while retaining the suture loop about the distal housing of the needle exchange device;
retracting tissue into a path between the needle and the needle exchange device;
f) rotating the needle holder arm with needle in the first direction, through the retracted tissue and into engagement with the needle exchange device;
rotating the needle holder arm in the second direction and to release the needle from engagement with the needle holder arm; and
releasing the needle from the needle exchange device, wherein the needle is positioned through the tissue and the suture loop such that the needle is retained on the tissue by the suture loop.

20. The method of claim 19, further comprising advancing the suture loop of the needle over an elongate suture extending through the working channel, wherein a distal end of the elongate suture is coupled to the tissue and a proximal end of the elongate suture extends out of the proximal end of the working channel.

* * * * *